United States Patent
Santos et al.

(10) Patent No.: US 7,682,601 B2
(45) Date of Patent: Mar. 23, 2010

(54) BIFUNCTIONAL TRIDENTATE PYRAZOLYL CONTAINING LIGANDS FOR RE AND TC TRICARBONYL COMPLEXES

(75) Inventors: Isabel Rego Santos, Lisbon (PT); Joao Domingos Galamba Correia, Lisbon (PT); Antonio Manuel Rocha Paulo, Liboa (PT); Susana Alves, Almada (PT); Rute Vitor, Santa Iria Da Azoia (PT)

(73) Assignee: Mallinckrodt Inc., Hazelwood, MO (US)

( * ) Notice: Subject to any disclaimer, the term of this patent is extended or adjusted under 35 U.S.C. 154(b) by 37 days.

(21) Appl. No.: 10/551,292

(22) PCT Filed: Apr. 15, 2004

(86) PCT No.: PCT/US2004/011685

§ 371 (c)(1),
(2), (4) Date: Sep. 28, 2005

(87) PCT Pub. No.: WO2004/091669

PCT Pub. Date: Oct. 28, 2004

(65) Prior Publication Data

US 2006/0198785 A1 Sep. 7, 2006

(30) Foreign Application Priority Data

Apr. 15, 2003 (EP) ................................... 03076106
Oct. 10, 2003 (EP) ................................... 03078217

(51) Int. Cl.
*A61K 51/00* (2006.01)
*A61M 36/14* (2006.01)

(52) U.S. Cl. ..................... 424/1.53; 424/1.11; 424/1.41; 424/1.45; 424/1.49; 424/1.65; 424/1.69; 424/1.73

(58) Field of Classification Search ................ 424/1.53, 424/1.11, 1.65, 1.69, 1.37, 1.41, 1.45, 1.49; 530/400, 409; 534/14; 536/23.32; 548/375.1
See application file for complete search history.

(56) References Cited

U.S. PATENT DOCUMENTS 5,066,479 A * 11/1991 Hawthorne ................. 424/1.53
5,569,769 A * 10/1996 Merkle et al. ............. 548/373.1
6,344,178 B1    2/2002 Alberto et al.
6,488,909 B1    12/2002 Hilger et al.

FOREIGN PATENT DOCUMENTS

WO    WO 98/48848    11/1998
WO    WO 00/50086    8/2000
WO    WO 01/00637    1/2001

OTHER PUBLICATIONS

Alberto et al., Synthesis and structures of technetium . . . , Polyhedron vol. 17, No. 8, pp. 1303-1309, 1998.
Alberto et al., Trotec-1: A New High-Affinity Ligand for Labeling of the Dopamine Transporter, J. Med. Chem., vol. 41, No. 23, Nov. 5, 1998.
Alberto et al., First application of fac-[99mTc(OH2)3(CO)3]+ in . . . , J. Am. Chem. Soc., vol. 121, pp. 6076-6077, 1999.
Alberto et al., Organometallic 99mTc-Aquaion Labels Peptide . . . , J. Nucl. Med., vol. 40, pp. 1913-1917, 1999.
Schibli et al., In Vitro and in Vivo Evaluation of Bidentate, Water-Soluble . . . , Nucl. Med. and Biol., vol. 26, pp. 711-716, 1999.
Alberto et al., Chemical and Bilogical Characterization of Technetium(I) and . . . , Bioconjugate Chem., vol. 11, pp. 414-424, 2000.
Alberto et al., Influence of the Denticity of Ligand Systems on the in Vitro and in Vivo . . . , Bioconjugate Chem., vol. 11, pp. 345-351, 2000.
Alberto et al., Derivatization of Glucose and 2-Deoxyglucose for Transition Metal . . . , Chem. Eur. Journal, vol. 7, No. 9, pp. 1868-1873, 2001.
Alberto et al., Aqueous One-Pot Synthesis of Derivatized Cyclopentadienyl . . . , Agnew. Chem. Int. Ed., vol. 40, No. 16, pp. 3062-3066, 2001.
Alberto et al., Steps toward High Specific Activity labeling of Biomolecules for . . . , Bioconjugate Chem., vol. 13, pp. 750-756, 2002.
Santos et al., Re and Tc Complexes containing B-H—M Agostic Interactions . . . , J. Am. chem. Soc., vol. 122, pp. 11240-11241, 2000.
Santos et al., Re Tricarbvonyl Complexes with Ligands Containing P,N,N, and P,N, O Donor . . . , Inorg. Chem. vol. 40, pp. 5147-5151, 2001.
Santos et al., Coordination capabilities of pyrazolyl containing ligands towards the . . . , J. Chem. Soc. Dalton Trans., pp. 4714-4719, 2002.
Valliant et al., Carboranes as Ligands for the PReparation of Organometallic Tc and Re radiopharmaceuticals . . . , Inorg. Chem., vol. 41, No. 4, pp. 628-630, 2002.

(Continued)

*Primary Examiner*—Michael G Hartley
*Assistant Examiner*—Leah Schlientz

(57) ABSTRACT

The present invention relates to a chelating agent of the general formula: (I), wherein m is 0 or 1; X is $NR_4$ or S; Y is $SR_5$, $NHR_5$ or $P(R_5)_2$; $R_1$ and $R_3$ are the same or different and are selected from H, alkyl or aryl; $R_2$ is H, COOH, $NHR_6$ or $(CH_2)_n COOR_6$; $R_4$ is H, alkyl, aryl, $(CH_2)_n COOR_6$ or $(CH2)_n OR_6$; $R_5$ is H, alkyl, aryl, $(CH_2)_n COOR_6$ or $(CH_2)_n OR_6$, $R_6$ is H, alkyl or aryl; n is 1, 2, 3, 4, 5, 6, 7, 8, 9 or 10; and when $R_1=R_3=CH_3$, $R_2$, $R_4$ and $R_5$ are not all three H. The invention further relates to a method and kit for the preparation of radiolabeled biomolecules while using the chelating agent.

(I)

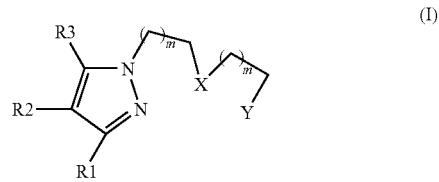

17 Claims, 8 Drawing Sheets

OTHER PUBLICATIONS

Valliant et al, Bifunctional Single Amino Acid Chelates for labeling of Biomoleucles with . . . , Inorg. Chem., vol. 41, No. 24, pp. 6417-6425, 2002.

Sorrell et al., Mononuclear Three-Coordinate Copper(I) Complexes: Synthesis, Structure, . . . , Inorg. Chem., vol. 22, pp. 1883-1887, 1983.

Driessen et al., Co-ordination Compounds with tyhe N2S-Donor Ligand 1,5-Bis . . . , J. Chem. Soc. Dalton Trans., pp. 481-486, 1992.

Parkin et al., Bis(pyrazolylethyl) Ether Ligation to zinc and Cobalt: Meridional vs Facial . . . , Inorg. Chem., vol. 35, pp. 2415-2420, 1996.

Ballesteros et al., N-2-(Azol-1(2)-yl)ethyliminodiacetic Acids: A Novel Series . . . , Bioorganic & Medicinal Chemistry 7, pp. 517-527, 1999.

Bouwman et al., Synthesis, characterization and crystal structures of nickel complexes with . . . , Inorg. Chim. Acta, vol. 310, pp. 183-190, 2000.

Holzer et al., N-1 Sustituted Ethyl 4-Pyrazolecarboxylates: Synthesis and Spectroscopic . . . , J. Heterocyclic Chem., vol. 30, pp. 865-872, 1993.

\* cited by examiner $X = NR_4, Y = NHR_5, SR_5, P(R_5)_2 ; X = S, Y = NHR_5; X = SR_5; P(R_5)_2$ BM = Biomolecule $R_1$-$R_5$ are as defined Table 1 a. NaOH 40% / TBAB; b. THF / H$_2$O / reflux / 4h; c. DMF, 0 °C, 3 h; d. CH$_3$CN / reflux / 3d; e. H$_2$O / .t. / 1d a. Ethanol, 0°C, overnight; b. NaOH, Acetone, H$_2$O, T.A., 3d; c. NaOH, THF, H$_2$O, reflux, 24h a. BOC-ON, THF, 0°C, 2h b. Ethyl 1-Bromobutyrate, K₂CO₃, KI, CH₃CN, r.t, 11d c. NaOH, H₂O, THF, reflux, overnight d. HBTU, NEt₃, CH₃CN, rt, 4h e. TFA, CH₂Cl₂, r.t, 1h a. mercaptoetanol, NaOH, THF/H₂O, reflux, 3h
b. PBr₃, CHCl₃, reflux, overnight
c. NaOH, H₂O, THF, reflux, overnight
d. Ethyl 2-mercaptoacetate, NaOEt, EtOH, r. t., overnight.

BIFUNCTIONAL TRIDENTATE PYRAZOLYL CONTAINING LIGANDS FOR RE AND TC TRICARBONYL COMPLEXES

CROSS-REFERENCE TO RELATED APPLICATION

This application is a National Stage application of PCT Application Serial No. PCT/US2004/011685, filed Apr. 15, 2004, which claims priority to EP 03076106.8, filed Apr. 15, 2003, and EP 03078217.1, filed Oct. 10, 2003.

This invention lies in the field of radiopharmaceuticals and provides new chelating agents to link biomolecules and carbonyl moieties for labeling with technetium and rhenium. In particular the invention relates to bifunctional tridentate pyrazolyl-polyamines, pyrazolyl-aminothioethers, pyrazolyl-polythioethers, pyrazolyl-aminophosphines and pyrazolyl-thioetherphosphines which stabilize the moieties $[M(CO)_3]^+$ (M=Re, Tc, Mn) and bind to biomolecules which accumulate in diseased tissues. The invention relates to the chelators as such, to chelators coupled to a biomolecule and to either of these complexed with carbonyl. In addition the invention relates to a kit for providing radiolabeled biomolecules and to the use of such radiolabeled molecules in diagnosis and therapy.

The diagnosis and therapy of cancer still needs a significant input from the chemical, radiochemical and pharmaceutical point of view. Tumour seeking compounds stable in vitro and in vivo, with high specific activity and specificity are still an important issue in the radiopharmaceutical field. Since the publication of international patents on $[Re(CO)_3]^+$ and $[Tc(CO)_3]^+$ [1] a significant interest has appeared in this oxidation state, which opens new perspectives on pharmaceutical and Nuclear Medicine fields. The search for new chelating agents is essential as they are determinant for the uptake of biological vectors. Several chelating agents have been described in patents [1, 2] and publications [3, 4, 5].

It is the object of the present invention to enlarge the family of bifunctional chelating agents.

This is achieved by the invention by chelating agents of the general formula:

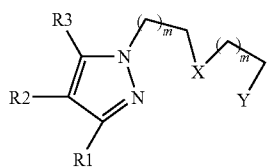

wherein m is 0 or 1;

X is $NR_4$ or S;

Y is $SR_5$, $NHR_5$ or $P(R_5)_2$;

$R_1$ and $R_3$ are the same or different and are selected from H, alkyl or aryl;

$R_2$ is H, COOH, $NHR_6$ or $(CH_2)_nCOOR_6$;

$R_4$ is H, alkyl, aryl, $(CH_2)_nCOOR_6$ or $(CH_2)_nOR_6$;

$R_5$ is H, alkyl, aryl, $(CH_2)_nCOOR_6$ or $(CH_2)_nOR_6$ $R_6$ is H, alkyl or aryl;

n is 1, 2, 3, 4, 5, 6, 7, 8, 9 or 10; and when $R_1$=$R_3$=$CH_3$, $R_2$, $R_4$ and $R_5$ are not all three H.

These molecules combine two functions. One is for the stabilization of metal centers, including radioactive metals, and comprises different donor atom sets, and the other is a functional group for binding to the molecule of interest.

The alkyl is a $C_1$ alkyl, $C_2$ alkyl, $C_3$ alkyl, $C_4$ alkyl, $C_5$ alkyl or $C_6$ alkyl, in particular selected from methyl, ethyl, n-propyl, isopropyl, n-butyl, isobutyl, s-butyl, t-butyl, n-pentyl, isopentyl, neopentyl, n-hexyl, isohexyl (2-methylpentyl), neohexyl (2,2-dimethylbutyl), 3-methylpentyl, 2,3-dimethylbutyl.

The aryls are monocyclic, $C_5$-$C_8$, or polycyclic $C_{10}$-$C_{18}$, and are optionally substituted with alkyl, carboxy, oxo, amino, alkoxy or aldehyde groups.

n is 2, 3, 4, 5 or 6 and preferably 2, 3 or 4.

The chelating agent is for example a pyrazolyl-polyamine of the general formula:

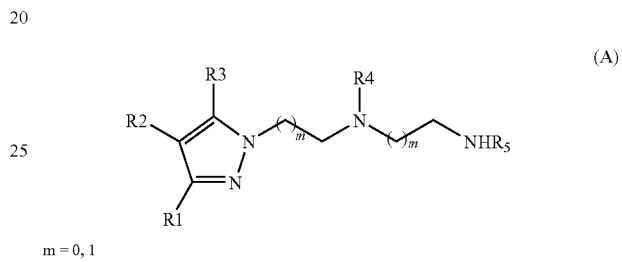

wherein $R_1$, $R_2$, $R_3$, $R_4$ and $R_5$ are as defined above.

Alternatively, the chelating agent is a pyrazolyl-aminothioether of the general formula:

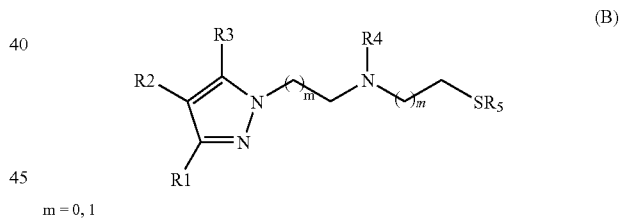

wherein $R_1$, $R_2$, $R_3$, $R_4$ and $R_5$ are as defined above.

In yet another embodiment the chelating agent is a pyrazolyl-polythioether of the general formula:

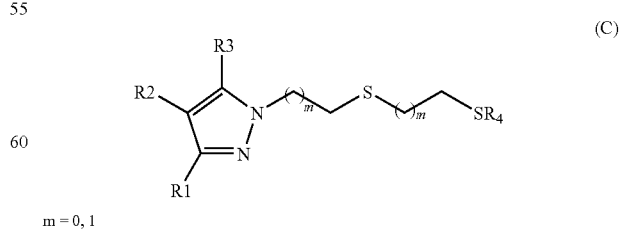

wherein $R_1$, $R_2$, $R_3$, $R_4$ and $R_5$ are as defined above.

In yet another embodiment the chelating agent is a pyrazolyl-aminophosphine of the general formula:

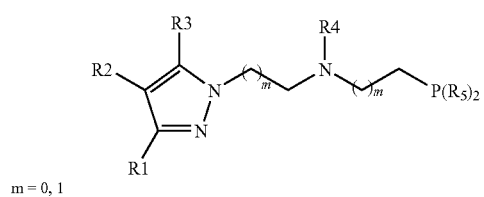

(D)

m = 0, 1 wherein $R_1$, $R_2$, $R_3$, $R_4$ and $R_5$ are as defined above.

In a further embodiment the chelating agent is a pyrazolyl-thioetherphosphine of the general formula:

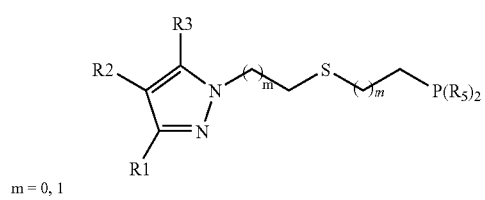

(E)

m = 0, 1 wherein $R_1$, $R_2$, $R_3$, $R_4$ and $R_5$ are as defined above.

The invention provides more particularly chelating agents of formula I, wherein X and Y are N, $R_6$ is H, $C_1$ alkyl, $C_2$ alkyl, $C_3$ alkyl, $C_4$ alkyl, $C_5$ alkyl or $C_6$ alkyl, monocyclic aryls, preferably phenyl or benzyl, or polycyclic $C_{10}$-$C_{18}$ aryls, optionally substituted with alkyl, carboxy, oxo, amino, alkoxy or aldehyde groups, or a biomolecule and $R_1$, $R_2$, $R_3$, $R_4$ and $R_5$ are as listed in Table 1.

In another embodiment the invention relates to chelating agents of formula I, wherein X and Y are S, $R_6$ is H, $C_1$ alkyl, $C_2$ alkyl, $C_3$ alkyl, $C_4$ alkyl, $C_5$ alkyl or $C_6$ alkyl, monocyclic aryls, preferably phenyl or benzyl, or polycyclic $C_{10}$-$C_{18}$ aryls, optionally substituted with alkyl, carboxy, oxo, amino, alkoxy or aldehyde groups, or a biomolecule and $R_1$, $R_2$, $R_3$, $R_4$ and $R_5$ are as listed in Table 1.

In yet another embodiment chelating agents of formula I are provided, wherein X is N and Y is S, $R_6$ is H, $C_1$ alkyl, $C_2$ alkyl, $C_3$ alkyl, $C_4$ alkyl, $C_5$ alkyl or $C_6$ alkyl, monocyclic aryls, preferably phenyl or benzyl, or polycyclic $C_{10}$-$C_{18}$ aryls, optionally substituted with alkyl, carboxy, oxo, amino, alkoxy or aldehyde groups, or a biomolecule and $R_1$, $R_2$, $R_3$, $R_4$ and $R_5$ are as listed in Table 1.

According to a further aspect thereof the invention relates to chelating agents of formula I, wherein X is S and Y are N, $R_6$ is H, $C_1$ alkyl, $C_2$ alkyl, $C_3$ alkyl, $C_4$ alkyl, $C_5$ alkyl or $C_6$ alkyl, monocyclic aryls, preferably phenyl or benzyl, or polycyclic $C_{10}$-$C_{18}$ aryls, optionally substituted with alkyl, carboxy, oxo, amino, alkoxy or aldehyde groups, or a biomolecule and $R_1$, $R_2$, $R_3$, $R_4$ and $R_5$ are as listed in Table 1.

According to another aspect of the invention, chelating agents of formula I are provided, wherein X is N and Y is P, $R_6$ is H, $C_1$ alkyl, $C_2$ alkyl, $C_3$ alkyl, $C_4$ alkyl, $C_5$ alkyl or $C_6$ alkyl, monocyclic aryls, preferably phenyl or benzyl, or polycyclic $C_{10}$-$C_{18}$ aryls, optionally substituted with alkyl, carboxy, oxo, amino, alkoxy or aldehyde groups, or a biomolecule and $R_1$, $R_2$, $R_3$, $R_4$ and $R_5$ are as listed in Table 1.

In another embodiment the invention relates to chelating agents of formula I, wherein X is S and Y is P, $R_6$ is H, $C_1$ alkyl, $C_2$ alkyl, $C_3$ alkyl, $C_4$ alkyl, $C_5$ alkyl or $C_6$ alkyl, monocyclic aryls, preferably phenyl or benzyl, or polycyclic $C_{10}$-$C_{18}$ aryls, optionally substituted with alkyl, carboxy, oxo, amino, alkoxy or aldehyde groups, or a biomolecule and $R_1$, $R_2$, $R_3$, $R_4$ and $R_5$ are as listed in Table 1.

The chelating agents of the invention are particularly suited to link biomolecules with carbonyl moieties in order to arrive at labeled biomolecules having a high specificity for the target. In formula I $R_6$ can thus be a biomolecule.

Figure 1:
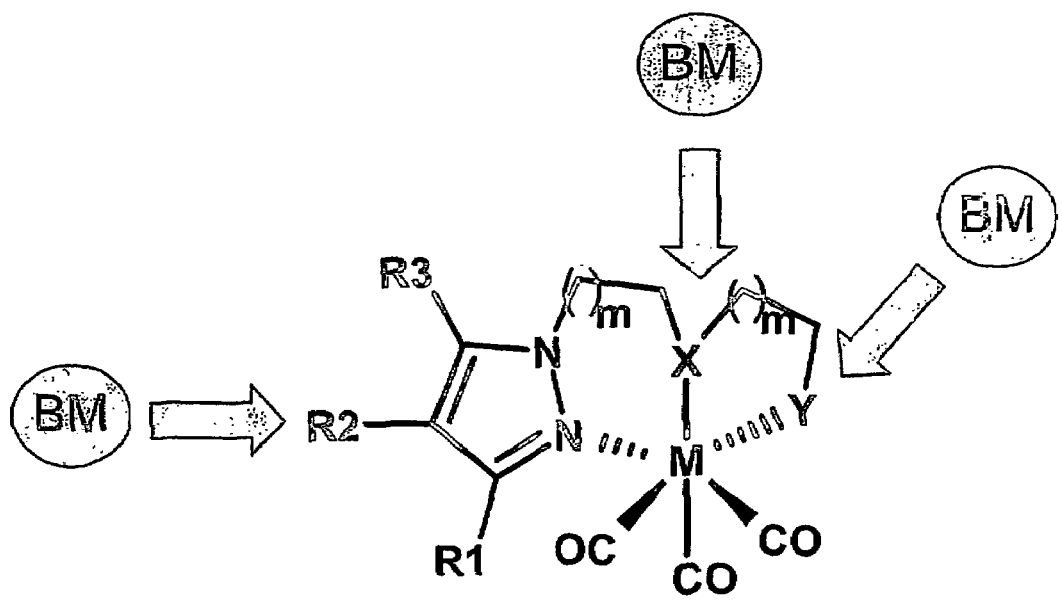
FIG. 1 depicts a chelating agent of one embodiment of the present disclosure with the possible positions of biomolecules being shown.

The possible positions of the biomolecules (BM) are shown in FIG. 1.

The biomolecule can be anything that is useful in the treatment and diagnosis of tumors and can be coupled to the chelators of the invention. The skilled person will be able to establish for which biomolecules the chelators of the invention can be used. In particular the biomolecule is selected from amino acids, peptides, proteins, oligonucleotides, polynucleotides, sugars.

More specifically, the biomolecule is selected from the group consisting of antibodies, ligands of tumor receptors, such as CCK, thioglucose, glucosamine, somatostatin, neurotensin, bombesin, CCK, annexin, interleukins, growth factors, steroid hormones and molecules binding to GPIIb/IIIa receptors. Other biomolecules can be glucose, thioglucose, neurotransmitters, inhibitors of the tyrosine kinase activity such as benzothiopyranones, anilinophthalimides, quinazolines, pyridopyrimidines and pyrrolopyrimidines.

Particular agents of the invention are the following:

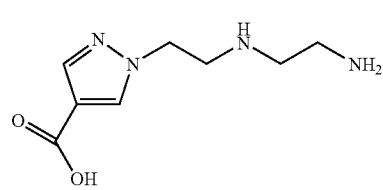

(7)

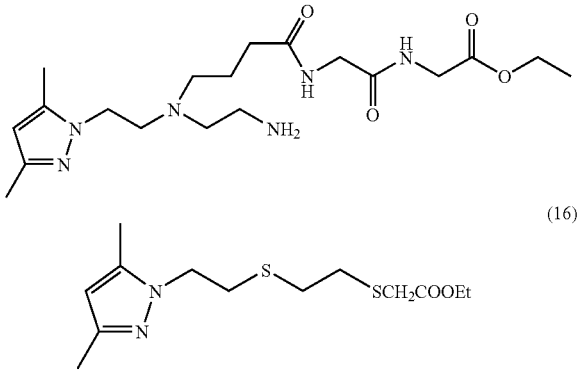

(13)

(16)

All of the chelating agents, either with or without a biomolecule coupled thereto can be complexed with a carbonyl moiety of the formula $[M(CO)_3]^+$, wherein M is rhenium (Re), technetium (Tc) or Manganese (Mn).

The chelating agents of the invention are molecules according to formula I wherein X and Y can be either N and N, N and S, S and N, S and S, N and P, or S and P. Each of these combinations can be combined with various combinations of $R_1$, $R_2$, $R_3$, $R_4$ and $R_5$. All possible combinations of $R_1$, $R_2$, $R_3$, $R_4$ and $R_5$ are listed in Table 1. In Table 1 alkyl is a $C_1$ alkyl, $C_2$ alkyl, $C_3$ alkyl, $C_4$ alkyl, $C_5$ alkyl or $C_6$ alkyl, in particular selected from methyl, ethyl, n-propyl, isopropyl, n-butyl, isobutyl, s-butyl, t-butyl, n-pentyl, isopentyl, neopentyl, n-hexyl, isohexyl (2-methylpentyl), neohexyl (2,2-dimethylbutyl), 3-methylpentyl, 2,3-dimethylbutyl; the aryl is monocyclic, $C_5$-$C_8$, or polycyclic, $C_{10}$-$C_{18}$, and optionally substituted with alkyl, carboxy, oxo, amino, alkoxy or aldehyde groups and is in particular phenyl or benzyl, and n is 1, 2, 3, 4, 5, 6, 7, 8, 9 or 10. $R_6$ is H, alkyl, aryl or a biomolecule as defined above. Substituting each of the above variables into the table will give all compounds of claim 1 that are herewith disclosed.

TABLE 1

| R1 | R2 | R3 | R4 | R5 |
|---|---|---|---|---|
| H | H | H | H | H |
| H | H | H | H | alkyl |
| H | H | H | H | aryl |
| H | H | H | H | $(CH_2)_n COOR_6$ |
| H | H | H | H | $(CH_2)_n OR_6$ |
| H | H | H | alkyl | H |
| H | H | H | alkyl | alkyl |
| H | H | H | alkyl | aryl |
| H | H | H | alkyl | $(CH_2)_n COOR_6$ |
| H | H | H | alkyl | $(CH_2)_n OR_6$ |
| H | H | H | aryl | H |
| H | H | H | aryl | alkyl |
| H | H | H | aryl | aryl |
| H | H | H | aryl | $(CH_2)_n COOR_6$ |
| H | H | H | aryl | $(CH_2)_n OR_6$ |
| H | H | H | $(CH_2)_n COOR_6$ | H |
| H | H | H | $(CH_2)_n COOR_6$ | alkyl |
| H | H | H | $(CH_2)_n COOR_6$ | aryl |
| H | H | H | $(CH_2)_n COOR_6$ | $(CH_2)_n COOR_6$ |
| H | H | H | $(CH_2)_n COOR_6$ | $(CH_2)_n OR_6$ |
| H | H | H | $(CH_2)_n OR_6$ | H |
| H | H | H | $(CH_2)_n OR_6$ | alkyl |
| H | H | H | $(CH_2)_n OR_6$ | aryl |
| H | H | H | $(CH_2)_n OR_6$ | $(CH_2)_n COOR_6$ |
| H | H | H | $(CH_2)_n OR_6$ | $(CH_2)_n OR_6$ |
| H | H | alkyl | H | H |
| H | H | alkyl | H | alkyl |
| H | H | alkyl | H | aryl |
| H | H | alkyl | H | $(CH_2)_n COOR_6$ |
| H | H | alkyl | H | $(CH_2)_n OR_6$ |
| H | H | alkyl | alkyl | H |
| H | H | alkyl | alkyl | alkyl |
| H | H | alkyl | alkyl | aryl |
| H | H | alkyl | alkyl | $(CH_2)_n COOR_6$ |
| H | H | alkyl | alkyl | $(CH_2)_n OR_6$ |
| H | H | alkyl | aryl | H |
| H | H | alkyl | aryl | alkyl |
| H | H | alkyl | aryl | aryl |
| H | H | alkyl | aryl | $(CH_2)_n COOR_6$ |
| H | H | alkyl | aryl | $(CH_2)_n OR_6$ |
| H | H | alkyl | $(CH_2)_n COOR_6$ | H |
| H | H | alkyl | $(CH_2)_n COOR_6$ | alkyl |
| H | H | alkyl | $(CH_2)_n COOR_6$ | aryl |
| H | H | alkyl | $(CH_2)_n COOR_6$ | $(CH_2)_n COOR_6$ |
| H | H | alkyl | $(CH_2)_n COOR_6$ | $(CH_2)_n OR_6$ |
| H | H | alkyl | $(CH_2)_n OR_6$ | H |
| H | H | alkyl | $(CH_2)_n OR_6$ | alkyl |
| H | H | alkyl | $(CH_2)_n OR_6$ | aryl |
| H | H | alkyl | $(CH_2)_n OR_6$ | $(CH_2)_n COOR_6$ |
| H | H | alkyl | $(CH_2)_n OR_6$ | $(CH_2)_n OR_6$ |
| H | H | aryl | H | H |
| H | H | aryl | H | alkyl |
| H | H | aryl | H | aryl |
| H | H | aryl | H | $(CH_2)_n COOR_6$ |
| H | H | aryl | H | $(CH_2)_n OR_6$ |
| H | H | aryl | alkyl | H |
| H | H | aryl | alkyl | alkyl |
| H | H | aryl | alkyl | aryl |
| H | H | aryl | alkyl | $(CH_2)_n COOR_6$ |
| H | H | aryl | alkyl | $(CH_2)_n OR_6$ |
| H | H | aryl | aryl | H |
| H | H | aryl | aryl | alkyl |
| H | H | aryl | aryl | aryl |
| H | H | aryl | aryl | $(CH_2)_n COOR_6$ |
| H | H | aryl | aryl | $(CH_2)_n OR_6$ |
| H | H | aryl | $(CH_2)_n COOR_6$ | H |
| H | H | aryl | $(CH_2)_n COOR_6$ | alkyl |
| H | H | aryl | $(CH_2)_n COOR_6$ | aryl |
| H | H | aryl | $(CH_2)_n COOR_6$ | $(CH_2)_n COOR_6$ |
| H | H | aryl | $(CH_2)_n COOR_6$ | $(CH_2)_n OR_6$ |
| H | H | aryl | $(CH_2)_n OR_6$ | H |
| H | H | aryl | $(CH_2)_n OR_6$ | alkyl |
| H | H | aryl | $(CH_2)_n OR_6$ | aryl |
| H | H | aryl | $(CH_2)_n OR_6$ | $(CH_2)_n COOR_6$ |
| H | H | aryl | $(CH_2)_n OR_6$ | $(CH_2)_n OR_6$ |
| H | COOH | H | H | H |
| H | COOH | H | H | alkyl |
| H | COOH | H | H | aryl |
| H | COOH | H | H | $(CH_2)_n COOR_6$ |
| H | COOH | H | H | $(CH_2)_n OR_6$ |
| H | COOH | H | alkyl | H |
| H | COOH | H | alkyl | alkyl |
| H | COOH | H | alkyl | aryl |
| H | COOH | H | alkyl | $(CH_2)_n COOR_6$ |
| H | COOH | H | alkyl | $(CH_2)_n OR_6$ |
| H | COOH | H | aryl | H |
| H | COOH | H | aryl | alkyl |
| H | COOH | H | aryl | aryl |
| H | COOH | H | aryl | $(CH_2)_n COOR_6$ |
| H | COOH | H | aryl | $(CH_2)_n OR_6$ |
| H | COOH | H | $(CH_2)_n COOR_6$ | H |
| H | COOH | H | $(CH_2)_n COOR_6$ | alkyl |
| H | COOH | H | $(CH_2)_n COOR_6$ | aryl |
| H | COOH | H | $(CH_2)_n COOR_6$ | $(CH_2)_n COOR_6$ |
| H | COOH | H | $(CH_2)_n COOR_6$ | $(CH_2)_n OR_6$ |
| H | COOH | H | $(CH_2)_n OR_6$ | H |
| H | COOH | H | $(CH_2)_n OR_6$ | alkyl |
| H | COOH | H | $(CH_2)_n OR_6$ | aryl |
| H | COOH | H | $(CH_2)_n OR_6$ | $(CH_2)_n COOR_6$ |
| H | COOH | H | $(CH_2)_n OR_6$ | $(CH_2)_n OR_6$ |
| H | COOH | alkyl | H | H |
| H | COOH | alkyl | H | alkyl |
| H | COOH | alkyl | H | aryl |

TABLE 1-continued

| R1 | R2 | R3 | R4 | R5 |
|---|---|---|---|---|
| H | COOH | alkyl | H | $(CH_2)_nCOOR_6$ |
| H | COOH | alkyl | H | $(CH_2)_nOR_6$ |
| H | COOH | alkyl | alkyl | H |
| H | COOH | alkyl | alkyl | alkyl |
| H | COOH | alkyl | alkyl | aryl |
| H | COOH | alkyl | alkyl | $(CH_2)_nCOOR_6$ |
| H | COOH | alkyl | alkyl | $(CH_2)_nOR_6$ |
| H | COOH | alkyl | aryl | H |
| H | COOH | alkyl | aryl | alkyl |
| H | COOH | alkyl | aryl | aryl |
| H | COOH | alkyl | aryl | $(CH_2)_nCOOR_6$ |
| H | COOH | alkyl | aryl | $(CH_2)_nOR_6$ |
| H | COOH | alkyl | $(CH_2)_nCOOR_6$ | H |
| H | COOH | alkyl | $(CH_2)_nCOOR_6$ | alkyl |
| H | COOH | alkyl | $(CH_2)_nCOOR_6$ | aryl |
| H | COOH | alkyl | $(CH_2)_nCOOR_6$ | $(CH_2)_nCOOR_6$ |
| H | COOH | alkyl | $(CH_2)_nCOOR_6$ | $(CH_2)_nOR_6$ |
| H | COOH | alkyl | $(CH_2)_nOR_6$ | H |
| H | COOH | alkyl | $(CH_2)_nOR_6$ | alkyl |
| H | COOH | alkyl | $(CH_2)_nOR_6$ | aryl |
| H | COOH | alkyl | $(CH_2)_nOR_6$ | $(CH_2)_nCOOR_6$ |
| H | COOH | alkyl | $(CH_2)_nOR_6$ | $(CH_2)_nOR_6$ |
| H | COOH | aryl | H | H |
| H | COOH | aryl | H | alkyl |
| H | COOH | aryl | H | aryl |
| H | COOH | aryl | H | $(CH_2)_nCOOR_6$ |
| H | COOH | aryl | H | $(CH_2)_nOR_6$ |
| H | COOH | aryl | alkyl | H |
| H | COOH | aryl | alkyl | alkyl |
| H | COOH | aryl | alkyl | aryl |
| H | COOH | aryl | alkyl | $(CH_2)_nCOOR_6$ |
| H | COOH | aryl | alkyl | $(CH_2)_nOR_6$ |
| H | COOH | aryl | aryl | H |
| H | COOH | aryl | aryl | alkyl |
| H | COOH | aryl | aryl | aryl |
| H | COOH | aryl | aryl | $(CH_2)_nCOOR_6$ |
| H | COOH | aryl | aryl | $(CH_2)_nOR_6$ |
| H | COOH | aryl | $(CH_2)_nCOOR_6$ | H |
| H | COOH | aryl | $(CH_2)_nCOOR_6$ | alkyl |
| H | COOH | aryl | $(CH_2)_nCOOR_6$ | aryl |
| H | COOH | aryl | $(CH_2)_nCOOR_6$ | $(CH_2)_nCOOR_6$ |
| H | COOH | aryl | $(CH_2)_nCOOR_6$ | $(CH_2)_nOR_6$ |
| H | COOH | aryl | $(CH_2)_nOR_6$ | H |
| H | COOH | aryl | $(CH_2)_nOR_6$ | alkyl |
| H | COOH | aryl | $(CH_2)_nOR_6$ | aryl |
| H | COOH | aryl | $(CH_2)_nOR_6$ | $(CH_2)_nCOOR_6$ |
| H | COOH | aryl | $(CH_2)_nOR_6$ | $(CH_2)_nOR_6$ |
| H | $NHR_6$ | H | H | H |
| H | $NHR_6$ | H | H | alkyl |
| H | $NHR_6$ | H | H | aryl |
| H | $NHR_6$ | H | H | $(CH_2)_nCOOR_6$ |
| H | $NHR_6$ | H | H | $(CH_2)_nOR_6$ |
| H | $NHR_6$ | H | alkyl | H |
| H | $NHR_6$ | H | alkyl | alkyl |
| H | $NHR_6$ | H | alkyl | aryl |
| H | $NHR_6$ | H | alkyl | $(CH_2)_nCOOR_6$ |
| H | $NHR_6$ | H | alkyl | $(CH_2)_nOR_6$ |
| H | $NHR_6$ | H | aryl | H |
| H | $NHR_6$ | H | aryl | alkyl |
| H | $NHR_6$ | H | aryl | aryl |
| H | $NHR_6$ | H | aryl | $(CH_2)_nCOOR_6$ |
| H | $NHR_6$ | H | aryl | $(CH_2)_nOR_6$ |
| H | $NHR_6$ | H | $(CH_2)_nCOOR_6$ | H |
| H | $NHR_6$ | H | $(CH_2)_nCOOR_6$ | alkyl |
| H | $NHR_6$ | H | $(CH_2)_nCOOR_6$ | aryl |
| H | $NHR_6$ | H | $(CH_2)_nCOOR_6$ | $(CH_2)_nCOOR_6$ |
| H | $NHR_6$ | H | $(CH_2)_nCOOR_6$ | $(CH_2)_nOR_6$ |
| H | $NHR_6$ | H | $(CH_2)_nOR_6$ | H |
| H | $NHR_6$ | H | $(CH_2)_nOR_6$ | alkyl |
| H | $NHR_6$ | H | $(CH_2)_nOR_6$ | aryl |
| H | $NHR_6$ | H | $(CH_2)_nOR_6$ | $(CH_2)_nCOOR_6$ |
| H | $NHR_6$ | H | $(CH_2)_nOR_6$ | $(CH_2)_nOR_6$ |
| H | $NHR_6$ | alkyl | H | H |
| H | $NHR_6$ | alkyl | H | alkyl |
| H | $NHR_6$ | alkyl | H | aryl |
| H | $NHR_6$ | alkyl | H | $(CH_2)_nCOOR_6$ |
| H | $NHR_6$ | alkyl | H | $(CH_2)_nOR_6$ |
| H | $NHR_6$ | alkyl | alkyl | H |
| H | $NHR_6$ | alkyl | alkyl | alkyl |
| H | $NHR_6$ | alkyl | alkyl | aryl |
| H | $NHR_6$ | alkyl | alkyl | $(CH_2)_nCOOR_6$ |
| H | $NHR_6$ | alkyl | alkyl | $(CH_2)_nOR_6$ |
| H | $NHR_6$ | alkyl | aryl | H |
| H | $NHR_6$ | alkyl | aryl | alkyl |
| H | $NHR_6$ | alkyl | aryl | aryl |
| H | $NHR_6$ | alkyl | aryl | $(CH_2)_nCOOR_6$ |
| H | $NHR_6$ | alkyl | aryl | $(CH_2)_nOR_6$ |
| H | $NHR_6$ | alkyl | $(CH_2)_nCOOR_6$ | H |
| H | $NHR_6$ | alkyl | $(CH_2)_nCOOR_6$ | alkyl |
| H | $NHR_6$ | alkyl | $(CH_2)_nCOOR_6$ | aryl |
| H | $NHR_6$ | alkyl | $(CH_2)_nCOOR_6$ | $(CH_2)_nCOOR_6$ |
| H | $NHR_6$ | alkyl | $(CH_2)_nCOOR_6$ | $(CH_2)_nOR_6$ |
| H | $NHR_6$ | alkyl | $(CH_2)_nOR_6$ | H |
| H | $NHR_6$ | alkyl | $(CH_2)_nOR_6$ | alkyl |
| H | $NHR_6$ | alkyl | $(CH_2)_nOR_6$ | aryl |
| H | $NHR_6$ | alkyl | $(CH_2)_nOR_6$ | $(CH_2)_nCOOR_6$ |
| H | $NHR_6$ | alkyl | $(CH_2)_nOR_6$ | $(CH_2)_nOR_6$ |
| H | $NHR_6$ | aryl | H | H |
| H | $NHR_6$ | aryl | H | alkyl |
| H | $NHR_6$ | aryl | H | aryl |
| H | $NHR_6$ | aryl | H | $(CH_2)_nCOOR_6$ |
| H | $NHR_6$ | aryl | H | $(CH_2)_nOR_6$ |
| H | $NHR_6$ | aryl | alkyl | H |
| H | $NHR_6$ | aryl | alkyl | alkyl |
| H | $NHR_6$ | aryl | alkyl | aryl |
| H | $NHR_6$ | aryl | alkyl | $(CH_2)_nCOOR_6$ |
| H | $NHR_6$ | aryl | alkyl | $(CH_2)_nOR_6$ |
| H | $NHR_6$ | aryl | aryl | H |
| H | $NHR_6$ | aryl | aryl | alkyl |
| H | $NHR_6$ | aryl | aryl | aryl |
| H | $NHR_6$ | aryl | aryl | $(CH_2)_nCOOR_6$ |
| H | $NHR_6$ | aryl | aryl | $(CH_2)_nOR_6$ |
| H | $NHR_6$ | aryl | $(CH_2)_nCOOR_6$ | H |
| H | $NHR_6$ | aryl | $(CH_2)_nCOOR_6$ | alkyl |
| H | $NHR_6$ | aryl | $(CH_2)_nCOOR_6$ | aryl |
| H | $NHR_6$ | aryl | $(CH_2)_nCOOR_6$ | $(CH_2)_nCOOR_6$ |
| H | $NHR_6$ | aryl | $(CH_2)_nCOOR_6$ | $(CH_2)_nOR_6$ |
| H | $NHR_6$ | aryl | $(CH_2)_nOR_6$ | H |
| H | $NHR_6$ | aryl | $(CH_2)_nOR_6$ | alkyl |
| H | $NHR_6$ | aryl | $(CH_2)_nOR_6$ | aryl |
| H | $NHR_6$ | aryl | $(CH_2)_nOR_6$ | $(CH_2)_nCOOR_6$ |
| H | $NHR_6$ | aryl | $(CH_2)_nOR_6$ | $(CH_2)_nOR_6$ |
| H | $(CH_2)_nCOOR_6$ | H | H | H |
| H | $(CH_2)_nCOOR_6$ | H | H | alkyl |
| H | $(CH_2)_nCOOR_6$ | H | H | aryl |
| H | $(CH_2)_nCOOR_6$ | H | H | $(CH_2)_nCOOR_6$ |
| H | $(CH_2)_nCOOR_6$ | H | H | $(CH_2)_nOR_6$ |
| H | $(CH_2)_nCOOR_6$ | H | alkyl | H |
| H | $(CH_2)_nCOOR_6$ | H | alkyl | alkyl |
| H | $(CH_2)_nCOOR_6$ | H | alkyl | aryl |
| H | $(CH_2)_nCOOR_6$ | H | alkyl | $(CH_2)_nCOOR_6$ |
| H | $(CH_2)_nCOOR_6$ | H | alkyl | $(CH_2)_nOR_6$ |
| H | $(CH_2)_nCOOR_6$ | H | aryl | H |
| H | $(CH_2)_nCOOR_6$ | H | aryl | alkyl |
| H | $(CH_2)_nCOOR_6$ | H | aryl | aryl |
| H | $(CH_2)_nCOOR_6$ | H | aryl | $(CH_2)_nCOOR_6$ |
| H | $(CH_2)_nCOOR_6$ | H | aryl | $(CH_2)_nOR_6$ |
| H | $(CH_2)_nCOOR_6$ | H | $(CH_2)_nCOOR_6$ | H |
| H | $(CH_2)_nCOOR_6$ | H | $(CH_2)_nCOOR_6$ | alkyl |
| H | $(CH_2)_nCOOR_6$ | H | $(CH_2)_nCOOR_6$ | aryl |
| H | $(CH_2)_nCOOR_6$ | H | $(CH_2)_nCOOR_6$ | $(CH_2)_nCOOR_6$ |
| H | $(CH_2)_nCOOR_6$ | H | $(CH_2)_nCOOR_6$ | $(CH_2)_nOR_6$ |
| H | $(CH_2)_nCOOR_6$ | H | $(CH_2)_nOR_6$ | H |
| H | $(CH_2)_nCOOR_6$ | H | $(CH_2)_nOR_6$ | alkyl |
| H | $(CH_2)_nCOOR_6$ | H | $(CH_2)_nOR_6$ | aryl |
| H | $(CH_2)_nCOOR_6$ | H | $(CH_2)_nOR_6$ | $(CH_2)_nCOOR_6$ |
| H | $(CH_2)_nCOOR_6$ | H | $(CH_2)_nOR_6$ | $(CH_2)_nOR_6$ |
| H | $(CH_2)_nCOOR_6$ | alkyl | H | H |
| H | $(CH_2)_nCOOR_6$ | alkyl | H | alkyl |
| H | $(CH_2)_nCOOR_6$ | alkyl | H | aryl |
| H | $(CH_2)_nCOOR_6$ | alkyl | H | $(CH_2)_nCOOR_6$ |
| H | $(CH_2)_nCOOR_6$ | alkyl | H | $(CH_2)_nOR_6$ |
| H | $(CH_2)_nCOOR_6$ | alkyl | alkyl | H |
| H | $(CH_2)_nCOOR_6$ | alkyl | alkyl | alkyl |

TABLE 1-continued

| R1 | R2 | R3 | R4 | R5 |
|---|---|---|---|---|
| H | $(CH_2)_n COOR_6$ | alkyl | alkyl | aryl |
| H | $(CH_2)_n COOR_6$ | alkyl | alkyl | $(CH_2)_n COOR_6$ |
| H | $(CH_2)_n COOR_6$ | alkyl | alkyl | $(CH_2)_n OR_6$ |
| H | $(CH_2)_n COOR_6$ | alkyl | aryl | H |
| H | $(CH_2)_n COOR_6$ | alkyl | aryl | alkyl |
| H | $(CH_2)_n COOR_6$ | alkyl | aryl | aryl |
| H | $(CH_2)_n COOR_6$ | alkyl | aryl | $(CH_2)_n COOR_6$ |
| H | $(CH_2)_n COOR_6$ | alkyl | aryl | $(CH_2)_n OR_6$ |
| H | $(CH_2)_n COOR_6$ | alkyl | $(CH_2)_n COOR_6$ | H |
| H | $(CH_2)_n COOR_6$ | alkyl | $(CH_2)_n COOR_6$ | alkyl |
| H | $(CH_2)_n COOR_6$ | alkyl | $(CH_2)_n COOR_6$ | aryl |
| H | $(CH_2)_n COOR_6$ | alkyl | $(CH_2)_n COOR_6$ | $(CH_2)_n COOR_6$ |
| H | $(CH_2)_n COOR_6$ | alkyl | $(CH_2)_n COOR_6$ | $(CH_2)_n OR_6$ |
| H | $(CH_2)_n COOR_6$ | alkyl | $(CH_2)_n OR_6$ | H |
| H | $(CH_2)_n COOR_6$ | alkyl | $(CH_2)_n OR_6$ | alkyl |
| H | $(CH_2)_n COOR_6$ | alkyl | $(CH_2)_n OR_6$ | aryl |
| H | $(CH_2)_n COOR_6$ | alkyl | $(CH_2)_n OR_6$ | $(CH_2)_n COOR_6$ |
| H | $(CH_2)_n COOR_6$ | alkyl | $(CH_2)_n OR_6$ | $(CH_2)_n OR_6$ |
| H | $(CH_2)_n COOR_6$ | aryl | H | H |
| H | $(CH_2)_n COOR_6$ | aryl | H | alkyl |
| H | $(CH_2)_n COOR_6$ | aryl | H | aryl |
| H | $(CH_2)_n COOR_6$ | aryl | H | $(CH_2)_n COOR_6$ |
| H | $(CH_2)_n COOR_6$ | aryl | H | $(CH_2)_n OR_6$ |
| H | $(CH_2)_n COOR_6$ | aryl | alkyl | H |
| H | $(CH_2)_n COOR_6$ | aryl | alkyl | alkyl |
| H | $(CH_2)_n COOR_6$ | aryl | alkyl | aryl |
| H | $(CH_2)_n COOR_6$ | aryl | alkyl | $(CH_2)_n COOR_6$ |
| H | $(CH_2)_n COOR_6$ | aryl | alkyl | $(CH_2)_n OR_6$ |
| H | $(CH_2)_n COOR_6$ | aryl | aryl | H |
| H | $(CH_2)_n COOR_6$ | aryl | aryl | alkyl |
| H | $(CH_2)_n COOR_6$ | aryl | aryl | aryl |
| H | $(CH_2)_n COOR_6$ | aryl | aryl | $(CH_2)_n COOR_6$ |
| H | $(CH_2)_n COOR_6$ | aryl | aryl | $(CH_2)_n OR_6$ |
| H | $(CH_2)_n COOR_6$ | aryl | $(CH_2)_n COOR_6$ | H |
| H | $(CH_2)_n COOR_6$ | aryl | $(CH_2)_n COOR_6$ | alkyl |
| H | $(CH_2)_n COOR_6$ | aryl | $(CH_2)_n COOR_6$ | aryl |
| H | $(CH_2)_n COOR_6$ | aryl | $(CH_2)_n COOR_6$ | $(CH_2)_n COOR_6$ |
| H | $(CH_2)_n COOR_6$ | aryl | $(CH_2)_n COOR_6$ | $(CH_2)_n OR_6$ |
| H | $(CH_2)_n COOR_6$ | aryl | $(CH_2)_n OR_6$ | H |
| H | $(CH_2)_n COOR_6$ | aryl | $(CH_2)_n OR_6$ | alkyl |
| H | $(CH_2)_n COOR_6$ | aryl | $(CH_2)_n OR_6$ | aryl |
| H | $(CH_2)_n COOR_6$ | aryl | $(CH_2)_n OR_6$ | $(CH_2)_n COOR_6$ |
| H | $(CH_2)_n COOR_6$ | aryl | $(CH_2)_n OR_6$ | $(CH_2)_n OR_6$ |
| alkyl | H | H | H | H |
| alkyl | H | H | H | alkyl |
| alkyl | H | H | H | aryl |
| alkyl | H | H | H | $(CH_2)_n COOR_6$ |
| alkyl | H | H | H | $(CH_2)_n OR_6$ |
| alkyl | H | H | alkyl | H |
| alkyl | H | H | alkyl | alkyl |
| alkyl | H | H | alkyl | aryl |
| alkyl | H | H | alkyl | $(CH_2)_n COOR_6$ |
| alkyl | H | H | alkyl | $(CH_2)_n OR_6$ |
| alkyl | H | H | aryl | H |
| alkyl | H | H | aryl | alkyl |
| alkyl | H | H | aryl | aryl |
| alkyl | H | H | aryl | $(CH_2)_n COOR_6$ |
| alkyl | H | H | aryl | $(CH_2)_n OR_6$ |
| alkyl | H | H | $(CH_2)_n COOR_6$ | H |
| alkyl | H | H | $(CH_2)_n COOR_6$ | alkyl |
| alkyl | H | H | $(CH_2)_n COOR_6$ | aryl |
| alkyl | H | H | $(CH_2)_n COOR_6$ | $(CH_2)_n COOR_6$ |
| alkyl | H | H | $(CH_2)_n COOR_6$ | $(CH_2)_n OR_6$ |
| alkyl | H | H | $(CH_2)_n OR_6$ | H |
| alkyl | H | H | $(CH_2)_n OR_6$ | alkyl |
| alkyl | H | H | $(CH_2)_n OR_6$ | aryl |
| alkyl | H | H | $(CH_2)_n OR_6$ | $(CH_2)_n COOR_6$ |
| alkyl | H | H | $(CH_2)_n OR_6$ | $(CH_2)_n OR_6$ |
| alkyl | H | alkyl | H | H |
| alkyl | H | alkyl | H | alkyl |
| alkyl | H | alkyl | H | aryl |
| alkyl | H | alkyl | H | $(CH_2)_n COOR_6$ |
| alkyl | H | alkyl | H | $(CH_2)_n OR_6$ |
| alkyl | H | alkyl | alkyl | H |
| alkyl | H | alkyl | alkyl | alkyl |
| alkyl | H | alkyl | alkyl | aryl |
| alkyl | H | alkyl | alkyl | $(CH_2)_n COOR_6$ |
| alkyl | H | alkyl | alkyl | $(CH_2)_n OR_6$ |
| alkyl | H | alkyl | aryl | H |
| alkyl | H | alkyl | aryl | alkyl |
| alkyl | H | alkyl | aryl | aryl |
| alkyl | H | alkyl | aryl | $(CH_2)_n COOR_6$ |
| alkyl | H | alkyl | aryl | $(CH_2)_n OR_6$ |
| alkyl | H | alkyl | $(CH_2)_n COOR_6$ | H |
| alkyl | H | alkyl | $(CH_2)_n COOR_6$ | alkyl |
| alkyl | H | alkyl | $(CH_2)_n COOR_6$ | aryl |
| alkyl | H | alkyl | $(CH_2)_n COOR_6$ | $(CH_2)_n COOR_6$ |
| alkyl | H | alkyl | $(CH_2)_n COOR_6$ | $(CH_2)_n OR_6$ |
| alkyl | H | alkyl | $(CH_2)_n OR_6$ | H |
| alkyl | H | alkyl | $(CH_2)_n OR_6$ | alkyl |
| alkyl | H | alkyl | $(CH_2)_n OR_6$ | aryl |
| alkyl | H | alkyl | $(CH_2)_n OR_6$ | $(CH_2)_n COOR_6$ |
| alkyl | H | alkyl | $(CH_2)_n OR_6$ | $(CH_2)_n OR_6$ |
| alkyl | H | aryl | H | H |
| alkyl | H | aryl | H | alkyl |
| alkyl | H | aryl | H | aryl |
| alkyl | H | aryl | H | $(CH_2)_n COOR_6$ |
| alkyl | H | aryl | H | $(CH_2)_n OR_6$ |
| alkyl | H | aryl | alkyl | H |
| alkyl | H | aryl | alkyl | alkyl |
| alkyl | H | aryl | alkyl | aryl |
| alkyl | H | aryl | alkyl | $(CH_2)_n COOR_6$ |
| alkyl | H | aryl | alkyl | $(CH_2)_n OR_6$ |
| alkyl | H | aryl | aryl | H |
| alkyl | H | aryl | aryl | alkyl |
| alkyl | H | aryl | aryl | aryl |
| alkyl | H | aryl | aryl | $(CH_2)_n COOR_6$ |
| alkyl | H | aryl | aryl | $(CH_2)_n OR_6$ |
| alkyl | H | aryl | $(CH_2)_n COOR_6$ | H |
| alkyl | H | aryl | $(CH_2)_n COOR_6$ | alkyl |
| alkyl | H | aryl | $(CH_2)_n COOR_6$ | aryl |
| alkyl | H | aryl | $(CH_2)_n COOR_6$ | $(CH_2)_n COOR_6$ |
| alkyl | H | aryl | $(CH_2)_n COOR_6$ | $(CH_2)_n OR_6$ |
| alkyl | H | aryl | $(CH_2)_n OR_6$ | H |
| alkyl | H | aryl | $(CH_2)_n OR_6$ | alkyl |
| alkyl | H | aryl | $(CH_2)_n OR_6$ | aryl |
| alkyl | H | aryl | $(CH_2)_n OR_6$ | $(CH_2)_n COOR_6$ |
| alkyl | H | aryl | $(CH_2)_n OR_6$ | $(CH_2)_n OR_6$ |
| alkyl | COOH | H | H | H |
| alkyl | COOH | H | H | alkyl |
| alkyl | COOH | H | H | aryl |
| alkyl | COOH | H | H | $(CH_2)_n COOR_6$ |
| alkyl | COOH | H | H | $(CH_2)_n OR_6$ |
| alkyl | COOH | H | alkyl | H |
| alkyl | COOH | H | alkyl | alkyl |
| alkyl | COOH | H | alkyl | aryl |
| alkyl | COOH | H | alkyl | $(CH_2)_n COOR_6$ |
| alkyl | COOH | H | alkyl | $(CH_2)_n OR_6$ |
| alkyl | COOH | H | aryl | H |
| alkyl | COOH | H | aryl | alkyl |
| alkyl | COOH | H | aryl | aryl |
| alkyl | COOH | H | aryl | $(CH_2)_n COOR_6$ |
| alkyl | COOH | H | aryl | $(CH_2)_n OR_6$ |
| alkyl | COOH | H | $(CH_2)_n COOR_6$ | H |
| alkyl | COOH | H | $(CH_2)_n COOR_6$ | alkyl |
| alkyl | COOH | H | $(CH_2)_n COOR_6$ | aryl |
| alkyl | COOH | H | $(CH_2)_n COOR_6$ | $(CH_2)_n COOR_6$ |
| alkyl | COOH | H | $(CH_2)_n COOR_6$ | $(CH_2)_n OR_6$ |
| alkyl | COOH | H | $(CH_2)_n OR_6$ | H |
| alkyl | COOH | H | $(CH_2)_n OR_6$ | alkyl |
| alkyl | COOH | H | $(CH_2)_n OR_6$ | aryl |
| alkyl | COOH | H | $(CH_2)_n OR_6$ | $(CH_2)_n COOR_6$ |
| alkyl | COOH | H | $(CH_2)_n OR_6$ | $(CH_2)_n OR_6$ |
| alkyl | COOH | alkyl | H | H |
| alkyl | COOH | alkyl | H | alkyl |
| alkyl | COOH | alkyl | H | aryl |
| alkyl | COOH | alkyl | H | $(CH_2)_n COOR_6$ |
| alkyl | COOH | alkyl | H | $(CH_2)_n OR_6$ |
| alkyl | COOH | alkyl | alkyl | H |
| alkyl | COOH | alkyl | alkyl | alkyl |
| alkyl | COOH | alkyl | alkyl | aryl |
| alkyl | COOH | alkyl | alkyl | $(CH_2)_n COOR_6$ |
| alkyl | COOH | alkyl | alkyl | $(CH_2)_n OR_6$ |
| alkyl | COOH | alkyl | aryl | H |

TABLE 1-continued

| R1 | R2 | R3 | R4 | R5 |
|---|---|---|---|---|
| alkyl | COOH | alkyl | aryl | alkyl |
| alkyl | COOH | alkyl | aryl | aryl |
| alkyl | COOH | alkyl | aryl | $(CH_2)_n COOR_6$ |
| alkyl | COOH | alkyl | aryl | $(CH_2)_n OR_6$ |
| alkyl | COOH | alkyl | $(CH_2)_n COOR_6$ | H |
| alkyl | COOH | alkyl | $(CH_2)_n COOR_6$ | alkyl |
| alkyl | COOH | alkyl | $(CH_2)_n COOR_6$ | aryl |
| alkyl | COOH | alkyl | $(CH_2)_n COOR_6$ | $(CH_2)_n COOR_6$ |
| alkyl | COOH | alkyl | $(CH_2)_n COOR_6$ | $(CH_2)_n OR_6$ |
| alkyl | COOH | alkyl | $(CH_2)_n OR_6$ | H |
| alkyl | COOH | alkyl | $(CH_2)_n OR_6$ | alkyl |
| alkyl | COOH | alkyl | $(CH_2)_n OR_6$ | aryl |
| alkyl | COOH | alkyl | $(CH_2)_n OR_6$ | $(CH_2)_n COOR_6$ |
| alkyl | COOH | alkyl | $(CH_2)_n OR_6$ | $(CH_2)_n OR_6$ |
| alkyl | COOH | aryl | H | H |
| alkyl | COOH | aryl | H | alkyl |
| alkyl | COOH | aryl | H | aryl |
| alkyl | COOH | aryl | H | $(CH_2)_n COOR_6$ |
| alkyl | COOH | aryl | H | $(CH_2)_n OR_6$ |
| alkyl | COOH | aryl | alkyl | H |
| alkyl | COOH | aryl | alkyl | alkyl |
| alkyl | COOH | aryl | alkyl | aryl |
| alkyl | COOH | aryl | alkyl | $(CH_2)_n COOR_6$ |
| alkyl | COOH | aryl | alkyl | $(CH_2)_n OR_6$ |
| alkyl | COOH | aryl | aryl | H |
| alkyl | COOH | aryl | aryl | alkyl |
| alkyl | COOH | aryl | aryl | aryl |
| alkyl | COOH | aryl | aryl | $(CH_2)_n COOR_6$ |
| alkyl | COOH | aryl | aryl | $(CH_2)_n OR_6$ |
| alkyl | COOH | aryl | $(CH_2)_n COOR_6$ | H |
| alkyl | COOH | aryl | $(CH_2)_n COOR_6$ | alkyl |
| alkyl | COOH | aryl | $(CH_2)_n COOR_6$ | aryl |
| alkyl | COOH | aryl | $(CH_2)_n COOR_6$ | $(CH_2)_n COOR_6$ |
| alkyl | COOH | aryl | $(CH_2)_n COOR_6$ | $(CH_2)_n OR_6$ |
| alkyl | COOH | aryl | $(CH_2)_n OR_6$ | H |
| alkyl | COOH | aryl | $(CH_2)_n OR_6$ | alkyl |
| alkyl | COOH | aryl | $(CH_2)_n OR_6$ | aryl |
| alkyl | COOH | aryl | $(CH_2)_n OR_6$ | $(CH_2)_n COOR_6$ |
| alkyl | COOH | aryl | $(CH_2)_n OR_6$ | $(CH_2)_n OR_6$ |
| alkyl | $NHR_6$ | H | H | H |
| alkyl | $NHR_6$ | H | H | alkyl |
| alkyl | $NHR_6$ | H | H | aryl |
| alkyl | $NHR_6$ | H | H | $(CH_2)_n COOR_6$ |
| alkyl | $NHR_6$ | H | H | $(CH_2)_n OR_6$ |
| alkyl | $NHR_6$ | H | alkyl | H |
| alkyl | $NHR_6$ | H | alkyl | alkyl |
| alkyl | $NHR_6$ | H | alkyl | aryl |
| alkyl | $NHR_6$ | H | alkyl | $(CH_2)_n COOR_6$ |
| alkyl | $NHR_6$ | H | alkyl | $(CH_2)_n OR_6$ |
| alkyl | $NHR_6$ | H | aryl | H |
| alkyl | $NHR_6$ | H | aryl | alkyl |
| alkyl | $NHR_6$ | H | aryl | aryl |
| alkyl | $NHR_6$ | H | aryl | $(CH_2)_n COOR_6$ |
| alkyl | $NHR_6$ | H | aryl | $(CH_2)_n OR_6$ |
| alkyl | $NHR_6$ | H | $(CH_2)_n COOR_6$ | H |
| alkyl | $NHR_6$ | H | $(CH_2)_n COOR_6$ | alkyl |
| alkyl | $NHR_6$ | H | $(CH_2)_n COOR_6$ | aryl |
| alkyl | $NHR_6$ | H | $(CH_2)_n COOR_6$ | $(CH_2)_n COOR_6$ |
| alkyl | $NHR_6$ | H | $(CH_2)_n COOR_6$ | $(CH_2)_n OR_6$ |
| alkyl | $NHR_6$ | H | $(CH_2)_n OR_6$ | H |
| alkyl | $NHR_6$ | H | $(CH_2)_n OR_6$ | alkyl |
| alkyl | $NHR_6$ | H | $(CH_2)_n OR_6$ | aryl |
| alkyl | $NHR_6$ | H | $(CH_2)_n OR_6$ | $(CH_2)_n COOR_6$ |
| alkyl | $NHR_6$ | H | $(CH_2)_n OR_6$ | $(CH_2)_n OR_6$ |
| alkyl | $NHR_6$ | alkyl | H | H |
| alkyl | $NHR_6$ | alkyl | H | alkyl |
| alkyl | $NHR_6$ | alkyl | H | aryl |
| alkyl | $NHR_6$ | alkyl | H | $(CH_2)_n COOR_6$ |
| alkyl | $NHR_6$ | alkyl | H | $(CH_2)_n OR_6$ |
| alkyl | $NHR_6$ | alkyl | alkyl | H |
| alkyl | $NHR_6$ | alkyl | alkyl | alkyl |
| alkyl | $NHR_6$ | alkyl | alkyl | aryl |
| alkyl | $NHR_6$ | alkyl | alkyl | $(CH_2)_n COOR_6$ |
| alkyl | $NHR_6$ | alkyl | alkyl | $(CH_2)_n OR_6$ |
| alkyl | $NHR_6$ | alkyl | aryl | H |
| alkyl | $NHR_6$ | alkyl | aryl | alkyl |
| alkyl | $NHR_6$ | alkyl | aryl | aryl |
| alkyl | $NHR_6$ | alkyl | aryl | $(CH_2)_n COOR_6$ |
| alkyl | $NHR_6$ | alkyl | aryl | $(CH_2)_n OR_6$ |
| alkyl | $NHR_6$ | alkyl | $(CH_2)_n COOR_6$ | H |
| alkyl | $NHR_6$ | alkyl | $(CH_2)_n COOR_6$ | alkyl |
| alkyl | $NHR_6$ | alkyl | $(CH_2)_n COOR_6$ | aryl |
| alkyl | $NHR_6$ | alkyl | $(CH_2)_n COOR_6$ | $(CH_2)_n COOR_6$ |
| alkyl | $NHR_6$ | alkyl | $(CH_2)_n COOR_6$ | $(CH_2)_n OR_6$ |
| alkyl | $NHR_6$ | alkyl | $(CH_2)_n OR_6$ | H |
| alkyl | $NHR_6$ | alkyl | $(CH_2)_n OR_6$ | alkyl |
| alkyl | $NHR_6$ | alkyl | $(CH_2)_n OR_6$ | aryl |
| alkyl | $NHR_6$ | alkyl | $(CH_2)_n OR_6$ | $(CH_2)_n COOR_6$ |
| alkyl | $NHR_6$ | alkyl | $(CH_2)_n OR_6$ | $(CH_2)_n OR_6$ |
| alkyl | $NHR_6$ | aryl | H | H |
| alkyl | $NHR_6$ | aryl | H | alkyl |
| alkyl | $NHR_6$ | aryl | H | aryl |
| alkyl | $NHR_6$ | aryl | H | $(CH_2)_n COOR_6$ |
| alkyl | $NHR_6$ | aryl | H | $(CH_2)_n OR_6$ |
| alkyl | $NHR_6$ | aryl | alkyl | H |
| alkyl | $NHR_6$ | aryl | alkyl | alkyl |
| alkyl | $NHR_6$ | aryl | alkyl | aryl |
| alkyl | $NHR_6$ | aryl | alkyl | $(CH_2)_n COOR_6$ |
| alkyl | $NHR_6$ | aryl | alkyl | $(CH_2)_n OR_6$ |
| alkyl | $NHR_6$ | aryl | aryl | H |
| alkyl | $NHR_6$ | aryl | aryl | alkyl |
| alkyl | $NHR_6$ | aryl | aryl | aryl |
| alkyl | $NHR_6$ | aryl | aryl | $(CH_2)_n COOR_6$ |
| alkyl | $NHR_6$ | aryl | aryl | $(CH_2)_n OR_6$ |
| alkyl | $NHR_6$ | aryl | $(CH_2)_n COOR_6$ | H |
| alkyl | $NHR_6$ | aryl | $(CH_2)_n COOR_6$ | alkyl |
| alkyl | $NHR_6$ | aryl | $(CH_2)_n COOR_6$ | aryl |
| alkyl | $NHR_6$ | aryl | $(CH_2)_n COOR_6$ | $(CH_2)_n COOR_6$ |
| alkyl | $NHR_6$ | aryl | $(CH_2)_n COOR_6$ | $(CH_2)_n OR_6$ |
| alkyl | $NHR_6$ | aryl | $(CH_2)_n OR_6$ | H |
| alkyl | $NHR_6$ | aryl | $(CH_2)_n OR_6$ | alkyl |
| alkyl | $NHR_6$ | aryl | $(CH_2)_n OR_6$ | aryl |
| alkyl | $NHR_6$ | aryl | $(CH_2)_n OR_6$ | $(CH_2)_n COOR_6$ |
| alkyl | $NHR_6$ | aryl | $(CH_2)_n OR_6$ | $(CH_2)_n OR_6$ |
| alkyl | $(CH_2)_n COOR_6$ | H | H | H |
| alkyl | $(CH_2)_n COOR_6$ | H | H | alkyl |
| alkyl | $(CH_2)_n COOR_6$ | H | H | aryl |
| alkyl | $(CH_2)_n COOR_6$ | H | H | $(CH_2)_n COOR_6$ |
| alkyl | $(CH_2)_n COOR_6$ | H | H | $(CH_2)_n OR_6$ |
| alkyl | $(CH_2)_n COOR_6$ | H | alkyl | H |
| alkyl | $(CH_2)_n COOR_6$ | H | alkyl | alkyl |
| alkyl | $(CH_2)_n COOR_6$ | H | alkyl | aryl |
| alkyl | $(CH_2)_n COOR_6$ | H | alkyl | $(CH_2)_n COOR_6$ |
| alkyl | $(CH_2)_n COOR_6$ | H | alkyl | $(CH_2)_n OR_6$ |
| alkyl | $(CH_2)_n COOR_6$ | H | aryl | H |
| alkyl | $(CH_2)_n COOR_6$ | H | aryl | alkyl |
| alkyl | $(CH_2)_n COOR_6$ | H | aryl | aryl |
| alkyl | $(CH_2)_n COOR_6$ | H | aryl | $(CH_2)_n COOR_6$ |
| alkyl | $(CH_2)_n COOR_6$ | H | aryl | $(CH_2)_n OR_6$ |
| alkyl | $(CH_2)_n COOR_6$ | H | $(CH_2)_n COOR_6$ | H |
| alkyl | $(CH_2)_n COOR_6$ | H | $(CH_2)_n COOR_6$ | alkyl |
| alkyl | $(CH_2)_n COOR_6$ | H | $(CH_2)_n COOR_6$ | aryl |
| alkyl | $(CH_2)_n COOR_6$ | H | $(CH_2)_n COOR_6$ | $(CH_2)_n COOR_6$ |
| alkyl | $(CH_2)_n COOR_6$ | H | $(CH_2)_n COOR_6$ | $(CH_2)_n OR_6$ |
| alkyl | $(CH_2)_n COOR_6$ | H | $(CH_2)_n OR_6$ | H |
| alkyl | $(CH_2)_n COOR_6$ | H | $(CH_2)_n OR_6$ | alkyl |
| alkyl | $(CH_2)_n COOR_6$ | H | $(CH_2)_n OR_6$ | aryl |
| alkyl | $(CH_2)_n COOR_6$ | H | $(CH_2)_n OR_6$ | $(CH_2)_n COOR_6$ |
| alkyl | $(CH_2)_n COOR_6$ | H | $(CH_2)_n OR_6$ | $(CH_2)_n OR_6$ |
| alkyl | $(CH_2)_n COOR_6$ | alkyl | H | H |
| alkyl | $(CH_2)_n COOR_6$ | alkyl | H | alkyl |
| alkyl | $(CH_2)_n COOR_6$ | alkyl | H | aryl |
| alkyl | $(CH_2)_n COOR_6$ | alkyl | H | $(CH_2)_n COOR_6$ |
| alkyl | $(CH_2)_n COOR_6$ | alkyl | H | $(CH_2)_n OR_6$ |
| alkyl | $(CH_2)_n COOR_6$ | alkyl | alkyl | H |
| alkyl | $(CH_2)_n COOR_6$ | alkyl | alkyl | alkyl |
| alkyl | $(CH_2)_n COOR_6$ | alkyl | alkyl | aryl |
| alkyl | $(CH_2)_n COOR_6$ | alkyl | alkyl | $(CH_2)_n COOR_6$ |
| alkyl | $(CH_2)_n COOR_6$ | alkyl | alkyl | $(CH_2)_n OR_6$ |
| alkyl | $(CH_2)_n COOR_6$ | alkyl | aryl | H |
| alkyl | $(CH_2)_n COOR_6$ | alkyl | aryl | alkyl |
| alkyl | $(CH_2)_n COOR_6$ | alkyl | aryl | aryl |
| alkyl | $(CH_2)_n COOR_6$ | alkyl | aryl | $(CH_2)_n COOR_6$ |
| alkyl | $(CH_2)_n COOR_6$ | alkyl | aryl | $(CH_2)_n OR_6$ |

TABLE 1-continued

| R1 | R2 | R3 | R4 | R5 |
|---|---|---|---|---|
| alkyl | $(CH_2)_nCOOR_6$ | alkyl | $(CH_2)_nCOOR_6$ | H |
| alkyl | $(CH_2)_nCOOR_6$ | alkyl | $(CH_2)_nCOOR_6$ | alkyl |
| alkyl | $(CH_2)_nCOOR_6$ | alkyl | $(CH_2)_nCOOR_6$ | aryl |
| alkyl | $(CH_2)_nCOOR_6$ | alkyl | $(CH_2)_nCOOR_6$ | $(CH_2)_nCOOR_6$ |
| alkyl | $(CH_2)_nCOOR_6$ | alkyl | $(CH_2)_nCOOR_6$ | $(CH_2)_nOR_6$ |
| alkyl | $(CH_2)_nCOOR_6$ | alkyl | $(CH_2)_nOR_6$ | H |
| alkyl | $(CH_2)_nCOOR_6$ | alkyl | $(CH_2)_nOR_6$ | alkyl |
| alkyl | $(CH_2)_nCOOR_6$ | alkyl | $(CH_2)_nOR_6$ | aryl |
| alkyl | $(CH_2)_nCOOR_6$ | alkyl | $(CH_2)_nOR_6$ | $(CH_2)_nCOOR_6$ |
| alkyl | $(CH_2)_nCOOR_6$ | alkyl | $(CH_2)_nCOR_6$ | $(CH_2)_nOR_6$ |
| alkyl | $(CH_2)_nCOOR_6$ | aryl | H | H |
| alkyl | $(CH_2)_nCOOR_6$ | aryl | H | alkyl |
| alkyl | $(CH_2)_nCOOR_6$ | aryl | H | aryl |
| alkyl | $(CH_2)_nCOOR_6$ | aryl | H | $(CH_2)_nCOOR_6$ |
| alkyl | $(CH_2)_nCOOR_6$ | aryl | H | $(CH_2)_nOR_6$ |
| alkyl | $(CH_2)_nCOOR_6$ | aryl | alkyl | H |
| alkyl | $(CH_2)_nCOOR_6$ | aryl | alkyl | alkyl |
| alkyl | $(CH_2)_nCOOR_6$ | aryl | alkyl | aryl |
| alkyl | $(CH_2)_nCOOR_6$ | aryl | alkyl | $(CH_2)_nCOOR_6$ |
| alkyl | $(CH_2)_nCOOR_6$ | aryl | alkyl | $(CH_2)_nOR_6$ |
| alkyl | $(CH_2)_nCOOR_6$ | aryl | aryl | H |
| alkyl | $(CH_2)_nCOOR_6$ | aryl | aryl | alkyl |
| alkyl | $(CH_2)_nCOOR_6$ | aryl | aryl | aryl |
| alkyl | $(CH_2)_nCOOR_6$ | aryl | aryl | $(CH_2)_nCOOR_6$ |
| alkyl | $(CH_2)_nCOOR_6$ | aryl | aryl | $(CH_2)_nOR_6$ |
| alkyl | $(CH_2)_nCOOR_6$ | aryl | $(CH_2)_nCOOR_6$ | H |
| alkyl | $(CH_2)_nCOOR_6$ | aryl | $(CH_2)_nCOOR_6$ | alkyl |
| alkyl | $(CH_2)_nCOOR_6$ | aryl | $(CH_2)_nCOOR_6$ | aryl |
| alkyl | $(CH_2)_nCOOR_6$ | aryl | $(CH_2)_nCOOR_6$ | $(CH_2)_nCOOR_6$ |
| alkyl | $(CH_2)_nCOOR_6$ | aryl | $(CH_2)_nCOOR_6$ | $(CH_2)_nOR_6$ |
| alkyl | $(CH_2)_nCOOR_6$ | aryl | $(CH_2)_nOR_6$ | H |
| alkyl | $(CH_2)_nCOOR_6$ | aryl | $(CH_2)_nOR_6$ | alkyl |
| alkyl | $(CH_2)_nCOOR_6$ | aryl | $(CH_2)_nOR_6$ | aryl |
| alkyl | $(CH_2)_nCOOR_6$ | aryl | $(CH_2)_nOR_6$ | $(CH_2)_nCOOR_6$ |
| alkyl | $(CH_2)_nCOOR_6$ | aryl | $(CH_2)_nOR_6$ | $(CH_2)_nOR_6$ |
| aryl | H | H | H | H |
| aryl | H | H | H | alkyl |
| aryl | H | H | H | aryl |
| aryl | H | H | H | $(CH_2)_nCOOR_6$ |
| aryl | H | H | H | $(CH_2)_nOR_6$ |
| aryl | H | H | alkyl | H |
| aryl | H | H | alkyl | alkyl |
| aryl | H | H | alkyl | aryl |
| aryl | H | H | alkyl | $(CH_2)_nCOOR_6$ |
| aryl | H | H | alkyl | $(CH_2)_nOR_6$ |
| aryl | H | H | aryl | H |
| aryl | H | H | aryl | alkyl |
| aryl | H | H | aryl | aryl |
| aryl | H | H | aryl | $(CH_2)_nCOOR_6$ |
| aryl | H | H | aryl | $(CH_2)_nOR_6$ |
| aryl | H | H | $(CH_2)_nCOOR_6$ | H |
| aryl | H | H | $(CH_2)_nCOOR_6$ | alkyl |
| aryl | H | H | $(CH_2)_nCOOR_6$ | aryl |
| aryl | H | H | $(CH_2)_nCOOR_6$ | $(CH_2)_nCOOR_6$ |
| aryl | H | H | $(CH_2)_nCOOR_6$ | $(CH_2)_nOR_6$ |
| aryl | H | H | $(CH_2)_nOR_6$ | H |
| aryl | H | H | $(CH_2)_nOR_6$ | alkyl |
| aryl | H | H | $(CH_2)_nOR_6$ | aryl |
| aryl | H | H | $(CH_2)_nOR_6$ | $(CH_2)_nCOOR_6$ |
| aryl | H | H | $(CH_2)_nOR_6$ | $(CH_2)_nOR_6$ |
| aryl | H | alkyl | H | H |
| aryl | H | alkyl | H | alkyl |
| aryl | H | alkyl | H | aryl |
| aryl | H | alkyl | H | $(CH_2)_nCOOR_6$ |
| aryl | H | alkyl | H | $(CH_2)_nOR_6$ |
| aryl | H | alkyl | alkyl | H |
| aryl | H | alkyl | alkyl | alkyl |
| aryl | H | alkyl | alkyl | aryl |
| aryl | H | alkyl | alkyl | $(CH_2)_nCOOR_6$ |
| aryl | H | alkyl | alkyl | $(CH_2)_nOR_6$ |
| aryl | H | alkyl | aryl | H |
| aryl | H | alkyl | aryl | alkyl |
| aryl | H | alkyl | aryl | aryl |
| aryl | H | alkyl | aryl | $(CH_2)_nCOOR_6$ |
| aryl | H | alkyl | aryl | $(CH_2)_nOR_6$ |
| aryl | H | alkyl | $(CH_2)_nCOOR_6$ | H |
| aryl | H | alkyl | $(CH_2)_nCOOR_6$ | alkyl |
| aryl | H | alkyl | $(CH_2)_nCOOR_6$ | aryl |
| aryl | H | alkyl | $(CH_2)_nCOOR_6$ | $(CH_2)_nCOOR_6$ |
| aryl | H | alkyl | $(CH_2)_nCOOR_6$ | $(CH_2)_nOR_6$ |
| aryl | H | alkyl | $(CH_2)_nOR_6$ | H |
| aryl | H | alkyl | $(CH_2)_nOR_6$ | alkyl |
| aryl | H | alkyl | $(CH_2)_nOR_6$ | aryl |
| aryl | H | alkyl | $(CH_2)_nOR_6$ | $(CH_2)_nCOOR_6$ |
| aryl | H | alkyl | $(CH_2)_nOR_6$ | $(CH_2)_nOR_6$ |
| aryl | H | aryl | H | H |
| aryl | H | aryl | H | alkyl |
| aryl | H | aryl | H | aryl |
| aryl | H | aryl | H | $(CH_2)_nCOOR_6$ |
| aryl | H | aryl | H | $(CH_2)_nOR_6$ |
| aryl | H | aryl | alkyl | H |
| aryl | H | aryl | alkyl | alkyl |
| aryl | H | aryl | alkyl | aryl |
| aryl | H | aryl | alkyl | $(CH_2)_nCOOR_6$ |
| aryl | H | aryl | alkyl | $(CH_2)_nOR_6$ |
| aryl | H | aryl | aryl | H |
| aryl | H | aryl | aryl | alkyl |
| aryl | H | aryl | aryl | aryl |
| aryl | H | aryl | aryl | $(CH_2)_nCOOR_6$ |
| aryl | H | aryl | aryl | $(CH_2)_nOR_6$ |
| aryl | H | aryl | $(CH_2)_nCOOR_6$ | H |
| aryl | H | aryl | $(CH_2)_nCOOR_6$ | alkyl |
| aryl | H | aryl | $(CH_2)_nCOOR_6$ | aryl |
| aryl | H | aryl | $(CH_2)_nCOOR_6$ | $(CH_2)_nCOOR_6$ |
| aryl | H | aryl | $(CH_2)_nCOOR_6$ | $(CH_2)_nOR_6$ |
| aryl | H | aryl | $(CH_2)_nOR_6$ | H |
| aryl | H | aryl | $(CH_2)_nOR_6$ | alkyl |
| aryl | H | aryl | $(CH_2)_nOR_6$ | aryl |
| aryl | H | aryl | $(CH_2)_nOR_6$ | $(CH_2)_nCOOR_6$ |
| aryl | H | aryl | $(CH_2)_nOR_6$ | $(CH_2)_nOR_6$ |
| aryl | COOH | H | H | H |
| aryl | COOH | H | H | alkyl |
| aryl | COOH | H | H | aryl |
| aryl | COOH | H | H | $(CH_2)_nCOOR_6$ |
| aryl | COOH | H | H | $(CH_2)_nOR_6$ |
| aryl | COOH | H | alkyl | H |
| aryl | COOH | H | alkyl | alkyl |
| aryl | COOH | H | alkyl | aryl |
| aryl | COOH | H | alkyl | $(CH_2)_nCOOR_6$ |
| aryl | COOH | H | alkyl | $(CH_2)_nOR_6$ |
| aryl | COOH | H | aryl | H |
| aryl | COOH | H | aryl | alkyl |
| aryl | COOH | H | aryl | aryl |
| aryl | COOH | H | aryl | $(CH_2)_nCOOR_6$ |
| aryl | COOH | H | aryl | $(CH_2)_nOR_6$ |
| aryl | COOH | H | $(CH_2)_nCOOR_6$ | H |
| aryl | COOH | H | $(CH_2)_nCOOR_6$ | alkyl |
| aryl | COOH | H | $(CH_2)_nCOOR_6$ | aryl |
| aryl | COOH | H | $(CH_2)_nCOOR_6$ | $(CH_2)_nCOOR_6$ |
| aryl | COOH | H | $(CH_2)_nCOOR_6$ | $(CH_2)_nOR_6$ |
| aryl | COOH | H | $(CH_2)_nOR_6$ | H |
| aryl | COOH | H | $(CH_2)_nOR_6$ | alkyl |
| aryl | COOH | H | $(CH_2)_nOR_6$ | aryl |
| aryl | COOH | H | $(CH_2)_nOR_6$ | $(CH_2)_nCOOR_6$ |
| aryl | COOH | H | $(CH_2)_nOR_6$ | $(CH_2)_nOR_6$ |
| aryl | COOH | alkyl | H | H |
| aryl | COOH | alkyl | H | alkyl |
| aryl | COOH | alkyl | H | aryl |
| aryl | COOH | alkyl | H | $(CH_2)_nCOOR_6$ |
| aryl | COOH | alkyl | H | $(CH_2)_nOR_6$ |
| aryl | COOH | alkyl | alkyl | H |
| aryl | COOH | alkyl | alkyl | alkyl |
| aryl | COOH | alkyl | alkyl | aryl |
| aryl | COOH | alkyl | alkyl | $(CH_2)_nCOOR_6$ |
| aryl | COOH | alkyl | alkyl | $(CH_2)_nOR_6$ |
| aryl | COOH | alkyl | aryl | H |
| aryl | COOH | alkyl | aryl | alkyl |
| aryl | COOH | alkyl | aryl | aryl |
| aryl | COOH | alkyl | aryl | $(CH_2)_nCOOR_6$ |
| aryl | COOH | alkyl | aryl | $(CH_2)_nOR_6$ |
| aryl | COOH | alkyl | $(CH_2)_nCOOR_6$ | H |
| aryl | COOH | alkyl | $(CH_2)_nCOOR_6$ | alkyl |
| aryl | COOH | alkyl | $(CH_2)_nCOOR_6$ | aryl |
| aryl | COOH | alkyl | $(CH_2)_nCOOR_6$ | $(CH_2)_nCOOR_6$ |

TABLE 1-continued

| R1 | R2 | R3 | R4 | R5 |
|---|---|---|---|---|
| aryl | COOH | alkyl | $(CH_2)_nCOOR_6$ | $(CH_2)_nOR_6$ |
| aryl | COOH | alkyl | $(CH_2)_nOR_6$ | H |
| aryl | COOH | alkyl | $(CH_2)_nOR_6$ | alkyl |
| aryl | COOH | alkyl | $(CH_2)_nOR_6$ | aryl |
| aryl | COOH | alkyl | $(CH_2)_nOR_6$ | $(CH_2)_nCOOR_6$ |
| aryl | COOH | alkyl | $(CH_2)_nOR_6$ | $(CH_2)_nOR_6$ |
| aryl | COOH | aryl | H | H |
| aryl | COOH | aryl | H | alkyl |
| aryl | COOH | aryl | H | aryl |
| aryl | COOH | aryl | H | $(CH_2)_nCOOR_6$ |
| aryl | COOH | aryl | H | $(CH_2)_nOR_6$ |
| aryl | COOH | aryl | alkyl | H |
| aryl | COOH | aryl | alkyl | alkyl |
| aryl | COOH | aryl | alkyl | aryl |
| aryl | COOH | aryl | alkyl | $(CH_2)_nCOOR_6$ |
| aryl | COOH | aryl | alkyl | $(CH_2)_nOR_6$ |
| aryl | COOH | aryl | aryl | H |
| aryl | COOH | aryl | aryl | alkyl |
| aryl | COOH | aryl | aryl | aryl |
| aryl | COOH | aryl | aryl | $(CH_2)_nCOOR_6$ |
| aryl | COOH | aryl | aryl | $(CH_2)_nOR_6$ |
| aryl | COOH | aryl | $(CH_2)_nCOOR_6$ | H |
| aryl | COOH | aryl | $(CH_2)_nCOOR_6$ | alkyl |
| aryl | COOH | aryl | $(CH_2)_nCOOR_6$ | aryl |
| aryl | COOH | aryl | $(CH_2)_nCOOR_6$ | $(CH_2)_nCOOR_6$ |
| aryl | COOH | aryl | $(CH_2)_nCOOR_6$ | $(CH_2)_nOR_6$ |
| aryl | COOH | aryl | $(CH_2)_nOR_6$ | H |
| aryl | COOH | aryl | $(CH_2)_nOR_6$ | alkyl |
| aryl | COOH | aryl | $(CH_2)_nOR_6$ | aryl |
| aryl | COOH | aryl | $(CH_2)_nOR_6$ | $(CH_2)_nCOOR_6$ |
| aryl | COOH | aryl | $(CH_2)_nOR_6$ | $(CH_2)_nOR_6$ |
| aryl | $NHR_6$ | H | H | H |
| aryl | $NHR_6$ | H | H | alkyl |
| aryl | $NHR_6$ | H | H | aryl |
| aryl | $NHR_6$ | H | H | $(CH_2)_nCOOR_6$ |
| aryl | $NHR_6$ | H | H | $(CH_2)_nOR_6$ |
| aryl | $NHR_6$ | H | alkyl | H |
| aryl | $NHR_6$ | H | alkyl | alkyl |
| aryl | $NHR_6$ | H | alkyl | aryl |
| aryl | $NHR_6$ | H | alkyl | $(CH_2)_nCOOR_6$ |
| aryl | $NHR_6$ | H | alkyl | $(CH_2)_nOR_6$ |
| aryl | $NHR_6$ | H | aryl | H |
| aryl | $NHR_6$ | H | aryl | alkyl |
| aryl | $NHR_6$ | H | aryl | aryl |
| aryl | $NHR_6$ | H | aryl | $(CH_2)_nCOOR_6$ |
| aryl | $NHR_6$ | H | aryl | $(CH_2)_nOR_6$ |
| aryl | $NHR_6$ | H | $(CH_2)_nCOOR_6$ | H |
| aryl | $NHR_6$ | H | $(CH_2)_nCOOR_6$ | alkyl |
| aryl | $NHR_6$ | H | $(CH_2)_nCOOR_6$ | aryl |
| aryl | $NHR_6$ | H | $(CH_2)_nCOOR_6$ | $(CH_2)_nCOOR_6$ |
| aryl | $NHR_6$ | H | $(CH_2)_nCOOR_6$ | $(CH_2)_nOR_6$ |
| aryl | $NHR_6$ | H | $(CH_2)_nOR_6$ | H |
| aryl | $NHR_6$ | H | $(CH_2)_nOR_6$ | alkyl |
| aryl | $NHR_6$ | H | $(CH_2)_nOR_6$ | aryl |
| aryl | $NHR_6$ | H | $(CH_2)_nOR_6$ | $(CH_2)_nCOOR_6$ |
| aryl | $NHR_6$ | H | $(CH_2)_nOR_6$ | $(CH_2)_nOR_6$ |
| aryl | $NHR_6$ | alkyl | H | H |
| aryl | $NHR_6$ | alkyl | H | alkyl |
| aryl | $NHR_6$ | alkyl | H | aryl |
| aryl | $NHR_6$ | alkyl | H | $(CH_2)_nCOOR_6$ |
| aryl | $NHR_6$ | alkyl | H | $(CH_2)_nOR_6$ |
| aryl | $NHR_6$ | alkyl | alkyl | H |
| aryl | $NHR_6$ | alkyl | alkyl | alkyl |
| aryl | $NHR_6$ | alkyl | alkyl | aryl |
| aryl | $NHR_6$ | alkyl | alkyl | $(CH_2)_nCOOR_6$ |
| aryl | $NHR_6$ | alkyl | alkyl | $(CH_2)_nOR_6$ |
| aryl | $NHR_6$ | alkyl | aryl | H |
| aryl | $NHR_6$ | alkyl | aryl | alkyl |
| aryl | $NHR_6$ | alkyl | aryl | aryl |
| aryl | $NHR_6$ | alkyl | aryl | $(CH_2)_nCOOR_6$ |
| aryl | $NHR_6$ | alkyl | aryl | $(CH_2)_nOR_6$ |
| aryl | $NHR_6$ | alkyl | $(CH_2)_nCOOR_6$ | H |
| aryl | $NHR_6$ | alkyl | $(CH_2)_nCOOR_6$ | alkyl |
| aryl | $NHR_6$ | alkyl | $(CH_2)_nCOOR_6$ | aryl |
| aryl | $NHR_6$ | alkyl | $(CH_2)_nCOOR_6$ | $(CH_2)_nCOOR_6$ |
| aryl | $NHR_6$ | alkyl | $(CH_2)_nCOOR_6$ | $(CH_2)_nOR_6$ |
| aryl | $NHR_6$ | alkyl | $(CH_2)_nOR_6$ | H |
| aryl | $NHR_6$ | alkyl | $(CH_2)_nOR_6$ | alkyl |
| aryl | $NHR_6$ | alkyl | $(CH_2)_nOR_6$ | aryl |
| aryl | $NHR_6$ | alkyl | $(CH_2)_nOR_6$ | $(CH_2)_nCOOR_6$ |
| aryl | $NHR_6$ | alkyl | $(CH_2)_nOR_6$ | $(CH_2)_nOR_6$ |
| aryl | $NHR_6$ | aryl | H | H |
| aryl | $NHR_6$ | aryl | H | alkyl |
| aryl | $NHR_6$ | aryl | H | aryl |
| aryl | $NHR_6$ | aryl | H | $(CH_2)_nCOOR_6$ |
| aryl | $NHR_6$ | aryl | H | $(CH_2)_nOR_6$ |
| aryl | $NHR_6$ | aryl | alkyl | H |
| aryl | $NHR_6$ | aryl | alkyl | alkyl |
| aryl | $NHR_6$ | aryl | alkyl | aryl |
| aryl | $NHR_6$ | aryl | alkyl | $(CH_2)_nCOOR_6$ |
| aryl | $NHR_6$ | aryl | alkyl | $(CH_2)_nOR_6$ |
| aryl | $NHR_6$ | aryl | aryl | H |
| aryl | $NHR_6$ | aryl | aryl | alkyl |
| aryl | $NHR_6$ | aryl | aryl | aryl |
| aryl | $NHR_6$ | aryl | aryl | $(CH_2)_nCOOR_6$ |
| aryl | $NHR_6$ | aryl | aryl | $(CH_2)_nOR_6$ |
| aryl | $NHR_6$ | aryl | $(CH_2)_nCOOR_6$ | H |
| aryl | $NHR_6$ | aryl | $(CH_2)_nCOOR_6$ | alkyl |
| aryl | $NHR_6$ | aryl | $(CH_2)_nCOOR_6$ | aryl |
| aryl | $NHR_6$ | aryl | $(CH_2)_nCOOR_6$ | $(CH_2)_nCOOR_6$ |
| aryl | $NHR_6$ | aryl | $(CH_2)_nCOOR_6$ | $(CH_2)_nOR_6$ |
| aryl | $NHR_6$ | aryl | $(CH_2)_nOR_6$ | H |
| aryl | $NHR_6$ | aryl | $(CH_2)_nOR_6$ | alkyl |
| aryl | $NHR_6$ | aryl | $(CH_2)_nOR_6$ | aryl |
| aryl | $NHR_6$ | aryl | $(CH_2)_nOR_6$ | $(CH_2)_nCOOR_6$ |
| aryl | $NHR_6$ | aryl | $(CH_2)_nOR_6$ | $(CH_2)_nOR_6$ |
| aryl | $(CH_2)_nCOOR_6$ | H | H | H |
| aryl | $(CH_2)_nCOOR_6$ | H | H | alkyl |
| aryl | $(CH_2)_nCOOR_6$ | H | H | aryl |
| aryl | $(CH_2)_nCOOR_6$ | H | H | $(CH_2)_nCOOR_6$ |
| aryl | $(CH_2)_nCOOR_6$ | H | H | $(CH_2)_nOR_6$ |
| aryl | $(CH_2)_nCOOR_6$ | H | alkyl | H |
| aryl | $(CH_2)_nCOOR_6$ | H | alkyl | alkyl |
| aryl | $(CH_2)_nCOOR_6$ | H | alkyl | aryl |
| aryl | $(CH_2)_nCOOR_6$ | H | alkyl | $(CH_2)_nCOOR_6$ |
| aryl | $(CH_2)_nCOOR_6$ | H | alkyl | $(CH_2)_nOR_6$ |
| aryl | $(CH_2)_nCOOR_6$ | H | aryl | H |
| aryl | $(CH_2)_nCOOR_6$ | H | aryl | alkyl |
| aryl | $(CH_2)_nCOOR_6$ | H | aryl | aryl |
| aryl | $(CH_2)_nCOOR_6$ | H | aryl | $(CH_2)_nCOOR_6$ |
| aryl | $(CH_2)_nCOOR_6$ | H | aryl | $(CH_2)_nOR_6$ |
| aryl | $(CH_2)_nCOOR_6$ | H | $(CH_2)_nCOOR_6$ | H |
| aryl | $(CH_2)_nCOOR_6$ | H | $(CH_2)_nCOOR_6$ | alkyl |
| aryl | $(CH_2)_nCOOR_6$ | H | $(CH_2)_nCOOR_6$ | aryl |
| aryl | $(CH_2)_nCOOR_6$ | H | $(CH_2)_nCOOR_6$ | $(CH_2)_nCOOR_6$ |
| aryl | $(CH_2)_nCOOR_6$ | H | $(CH_2)_nOR_6$ | H |
| aryl | $(CH_2)_nCOOR_6$ | H | $(CH_2)_nOR_6$ | alkyl |
| aryl | $(CH_2)_nCOOR_6$ | H | $(CH_2)_nOR_6$ | aryl |
| aryl | $(CH_2)_nCOOR_6$ | H | $(CH_2)_nOR_6$ | $(CH_2)_nOR_6$ |
| aryl | $(CH_2)_nCOOR_6$ | alkyl | H | H |
| aryl | $(CH_2)_nCOOR_6$ | alkyl | H | alkyl |
| aryl | $(CH_2)_nCOOR_6$ | alkyl | H | aryl |
| aryl | $(CH_2)_nCOOR_6$ | alkyl | H | $(CH_2)_nCOOR_6$ |
| aryl | $(CH_2)_nCOOR_6$ | alkyl | H | $(CH_2)_nOR_6$ |
| aryl | $(CH_2)_nCOOR_6$ | alkyl | alkyl | H |
| aryl | $(CH_2)_nCOOR_6$ | alkyl | alkyl | alkyl |
| aryl | $(CH_2)_nCOOR_6$ | alkyl | alkyl | aryl |
| aryl | $(CH_2)_nCOOR_6$ | alkyl | alkyl | $(CH_2)_nCOOR_6$ |
| aryl | $(CH_2)_nCOOR_6$ | alkyl | alkyl | $(CH_2)_nOR_6$ |
| aryl | $(CH_2)_nCOOR_6$ | alkyl | aryl | H |
| aryl | $(CH_2)_nCOOR_6$ | alkyl | aryl | alkyl |
| aryl | $(CH_2)_nCOOR_6$ | alkyl | aryl | aryl |
| aryl | $(CH_2)_nCOOR_6$ | alkyl | aryl | $(CH_2)_nCOOR_6$ |
| aryl | $(CH_2)_nCOOR_6$ | alkyl | aryl | $(CH_2)_nOR_6$ |
| aryl | $(CH_2)_nCOOR_6$ | alkyl | $(CH_2)_nCOOR_6$ | H |
| aryl | $(CH_2)_nCOOR_6$ | alkyl | $(CH_2)_nCOOR_6$ | alkyl |
| aryl | $(CH_2)_nCOOR_6$ | alkyl | $(CH_2)_nCOOR_6$ | aryl |
| aryl | $(CH_2)_nCOOR_6$ | alkyl | $(CH_2)_nCOOR_6$ | $(CH_2)_nCOOR_6$ |
| aryl | $(CH_2)_nCOOR_6$ | alkyl | $(CH_2)_nCOOR_6$ | $(CH_2)_nOR_6$ |
| aryl | $(CH_2)_nCOOR_6$ | alkyl | $(CH_2)_nOR_6$ | H |
| aryl | $(CH_2)_nCOOR_6$ | alkyl | $(CH_2)_nOR_6$ | alkyl |
| aryl | $(CH_2)_nCOOR_6$ | alkyl | $(CH_2)_nOR_6$ | aryl |

TABLE 1-continued

| R1 | R2 | R3 | R4 | R5 |
|---|---|---|---|---|
| aryl | (CH$_2$)$_n$COOR$_6$ | alkyl | (CH$_2$)$_n$OR$_6$ | (CH$_2$)$_n$COOR$_6$ |
| aryl | (CH$_2$)$_n$COOR$_6$ | alkyl | (CH$_2$)$_n$OR$_6$ | (CH$_2$)$_n$OR$_6$ |
| aryl | (CH$_2$)$_n$COOR$_6$ | aryl | H | H |
| aryl | (CH$_2$)$_n$COOR$_6$ | aryl | H | alkyl |
| aryl | (CH$_2$)$_n$COOR$_6$ | aryl | H | aryl |
| aryl | (CH$_2$)$_n$COOR$_6$ | aryl | H | (CH$_2$)$_n$COOR$_6$ |
| aryl | (CH$_2$)$_n$COOR$_6$ | aryl | H | (CH$_2$)$_n$OR$_6$ |
| aryl | (CH$_2$)$_n$COOR$_6$ | aryl | alkyl | H |
| aryl | (CH$_2$)$_n$COOR$_6$ | aryl | alkyl | alkyl |
| aryl | (CH$_2$)$_n$COOR$_6$ | aryl | alkyl | aryl |
| aryl | (CH$_2$)$_n$COOR$_6$ | aryl | alkyl | (CH$_2$)$_n$COOR$_6$ |
| aryl | (CH$_2$)$_n$COOR$_6$ | aryl | alkyl | (CH$_2$)$_n$OR$_6$ |
| aryl | (CH$_2$)$_n$COOR$_6$ | aryl | aryl | H |
| aryl | (CH$_2$)$_n$COOR$_6$ | aryl | aryl | alkyl |
| aryl | (CH$_2$)$_n$COOR$_6$ | aryl | aryl | aryl |
| aryl | (CH$_2$)$_n$COOR$_6$ | aryl | aryl | (CH$_2$)$_n$COOR$_6$ |
| aryl | (CH$_2$)$_n$COOR$_6$ | aryl | aryl | (CH$_2$)$_n$OR$_6$ |
| aryl | (CH$_2$)$_n$COOR$_6$ | aryl | (CH$_2$)$_n$COOR$_6$ | H |
| aryl | (CH$_2$)$_n$COOR$_6$ | aryl | (CH$_2$)$_n$COOR$_6$ | alkyl |
| aryl | (CH$_2$)$_n$COOR$_6$ | aryl | (CH$_2$)$_n$COOR$_6$ | aryl |
| aryl | (CH$_2$)$_n$COOR$_6$ | aryl | (CH$_2$)$_n$COOR$_6$ | (CH$_2$)$_n$COOR$_6$ |
| aryl | (CH$_2$)$_n$COOR$_6$ | aryl | (CH$_2$)$_n$COOR$_6$ | (CH$_2$)$_n$OR$_6$ |
| aryl | (CH$_2$)$_n$COOR$_6$ | aryl | (CH$_2$)$_n$OR$_6$ | H |
| aryl | (CH$_2$)$_n$COOR$_6$ | aryl | (CH$_2$)$_n$OR$_6$ | alkyl |
| aryl | (CH$_2$)$_n$COOR$_6$ | aryl | (CH$_2$)$_n$OR$_6$ | aryl |
| aryl | (CH$_2$)$_n$COOR$_6$ | aryl | (CH$_2$)$_n$OR$_6$ | (CH$_2$)$_n$COOR$_6$ |
| aryl | (CH$_2$)$_n$COOR$_6$ | aryl | (CH$_2$)$_n$OR$_6$ | (CH$_2$)$_n$OR$_6$ |

The invention also relates to a method for the preparation of radiolabeled biomolecules comprising:

a) contacting a chelating agent of the invention with a carbonyl moiety of the formula [M(CO)$_3$]$^+$, wherein M is rhenium (Re) or technetium (Tc), under conditions for forming a chelator-carbonyl complex; and b) contacting the complex with a biomolecule for obtaining a radiolabeled biomolecule. This method is in particular useful for labeling biomolecules that are sensitive to temperature and extreme pH.

This method can for example be performed with a kit, comprising a first vial with the chelating agent of the invention, optionally a first reaction vial for contacting the chelating agent with the carbonyl moiety, a second vial with the biomolecule and optionally a second reaction vial for reacting the biomolecule with the chelator-carbonyl complex obtained in the first step of the reaction.

In an alternative embodiment the invention provides a method for the preparation of radiolabeled biomolecules comprising:

a) contacting a chelating agent of the invention with a biomolecule for obtaining a chelator-biomolecule; and b) contacting the chelator-biomolecule with a carbonyl moiety of the formula [M(CO)$_3$]$^+$, wherein M is rhenium (Re) or technetium (Tc) under conditions for forming a radiolabeled biomolecule.

A kit for performing this method comprises for example a first vial with the chelating agent of the invention, optionally a first reaction vial for reacting the chelating agent with the biomolecule, a second vial with the carbonyl moiety and optionally a second reaction vial for reacting the chelator-biomolecule obtained in the first step of the reaction with the carbonyl.

The invention will be further illustrated in the example that follows.

EXAMPLE

Introduction

The bifunctional pyrazolyl-polyamines, pyrazolyl-polythioether, pyrazolyl amino-thioether ligands, pyrazolyl-aminophosphines and pyrazolyl-thioetherphosphines contain different donor atom sets to stabilize the metal and have different functional groups in different positions to which seeking molecules such as, for example, monoclonal antibodies, peptides, oligonucleotides and glycoproteins, can be coupled. They can also have different substituents and alkyl chains in different positions of the backbone for tuning the physico-chemical properties of the molecules.

Figure 2:
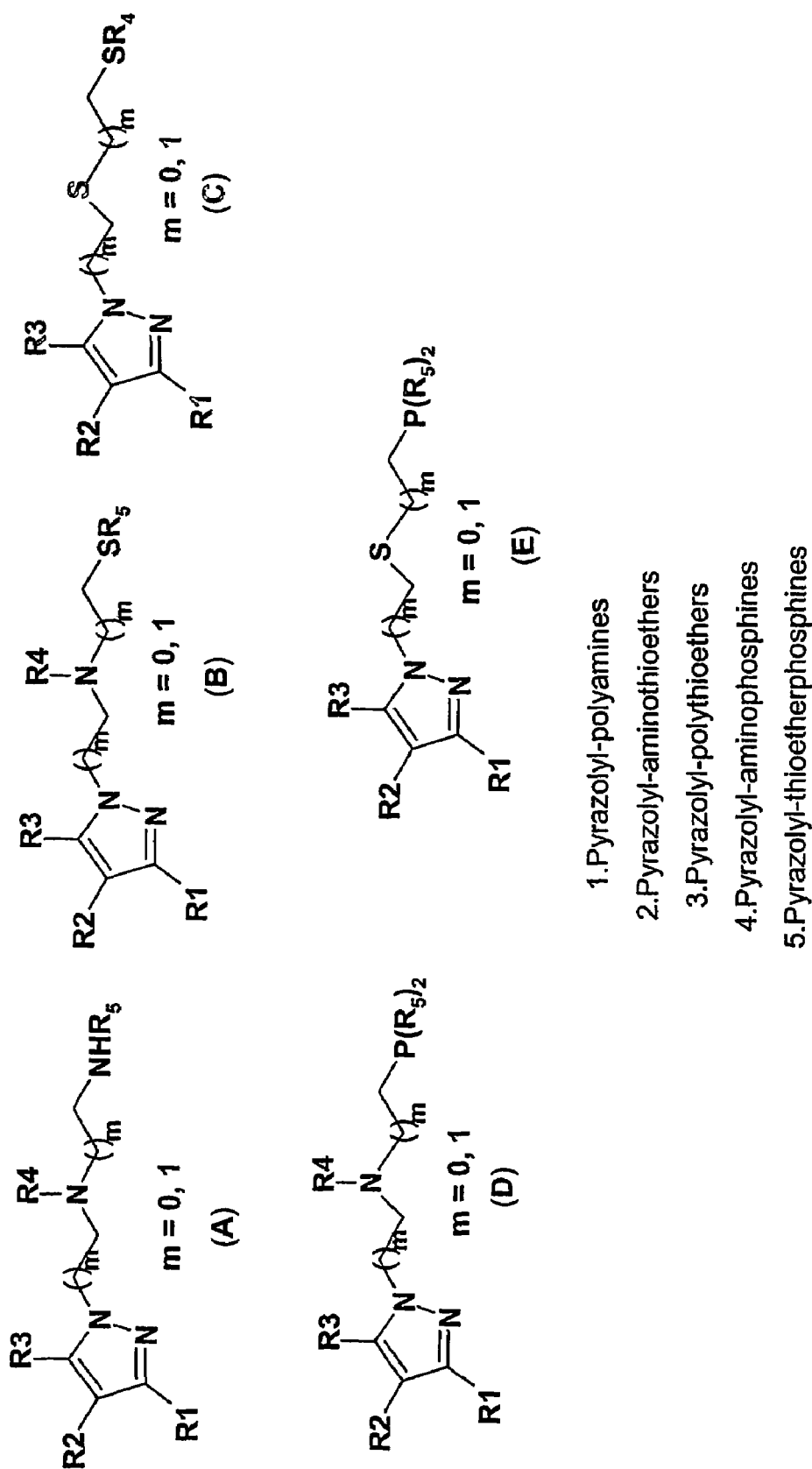
FIG. 2 depicts five embodiments of bifunctional tridentate pyrazolyl-containing ligands according to the present disclosure.
Figure 3:
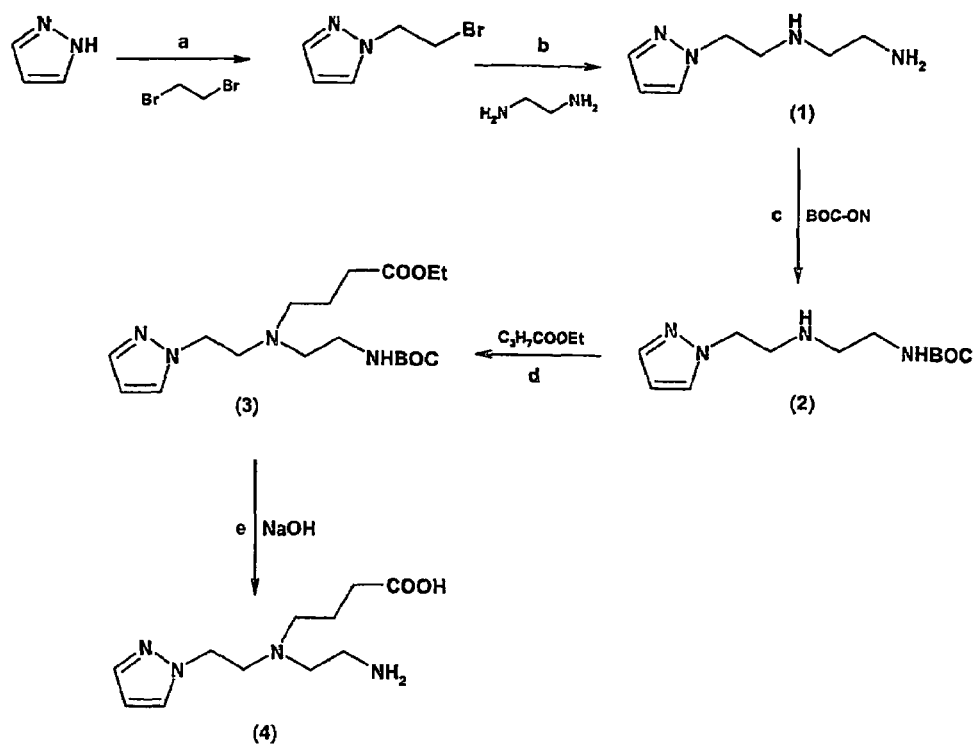
FIG. 3 is a schematic of a synthesis route for producing 2-[2-(pyrazol-1-yl)ethylimino]ethylamine ($pz(CH_2)_2NH(CH_2)_2NH_2$), $pz(CH_2)_2N[(CH_2)_3COOH](CH_2)_2NH_2$ and (4-carboxylic)$pz(CH_2)_2NH(CH_2)_2NH_2$ according to Examples 1-3.
Figure 3:
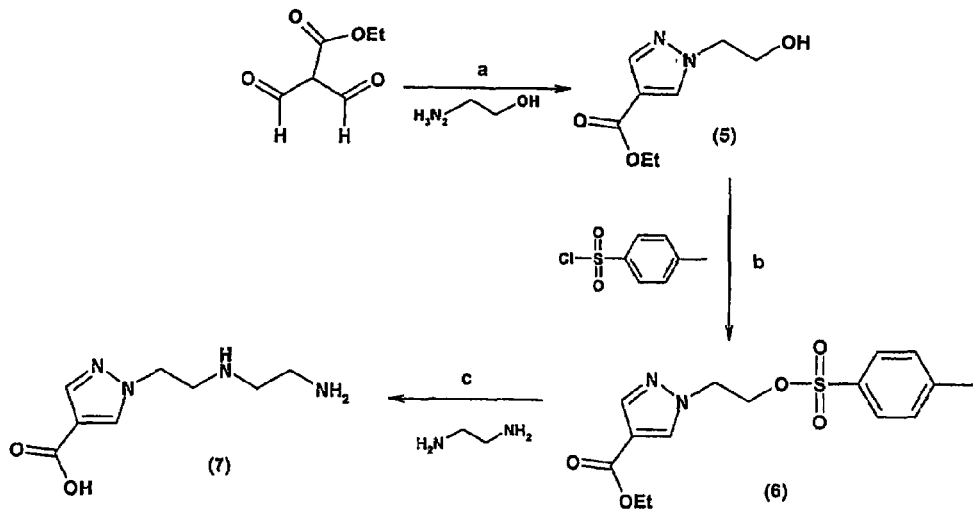

A general overview is given in FIG. 1, showing possible combinations for metal fragments of the type [M(CO)$_3$]$^+$ (M=Re, Tc, Mn). The five different types of bifunctional tridentate pyrazolyl-containing ligands, which are subject of this invention are depicted schematically in FIG. 2.

Figure 4:
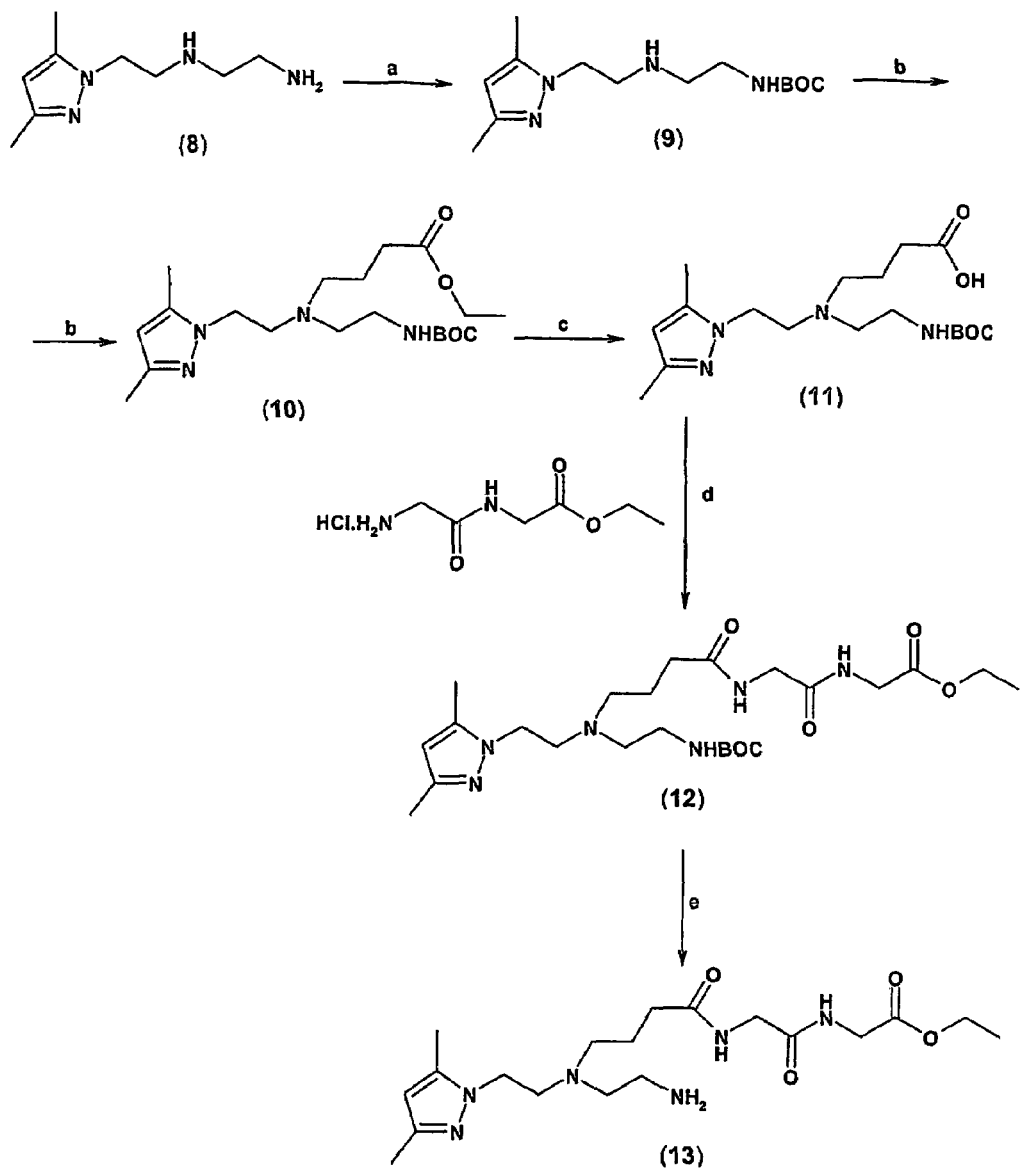
FIG. 4 is a schematic of a synthesis route for producing 3,5-Mepz$(CH_2)_2N[(CH_2)_3GlyGlyOEt)](CH_2)_2NH_2$ according to Example 4.
Figure 5:
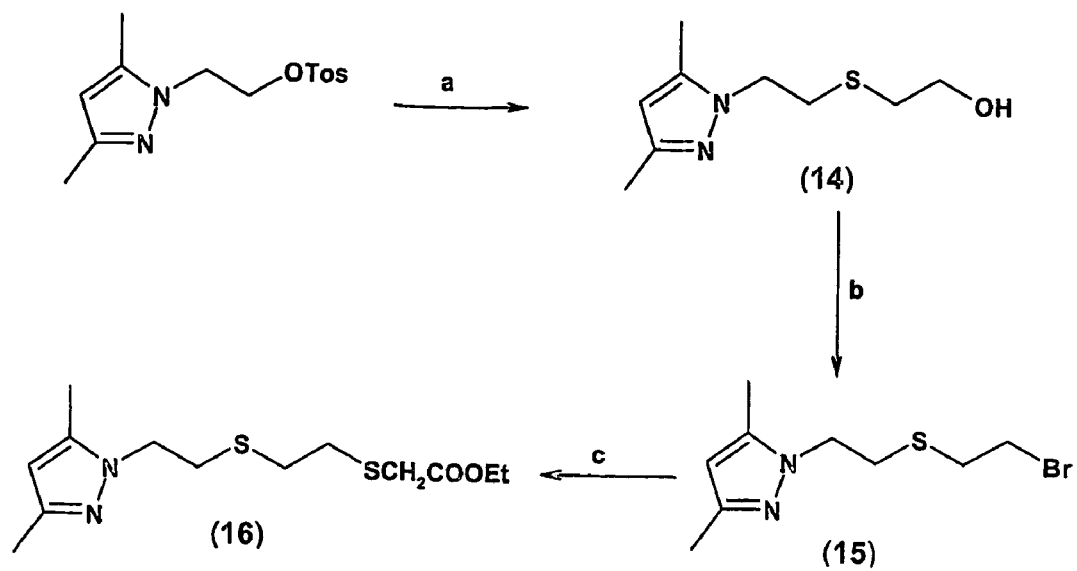
FIG. 5 is a schematic of a synthesis route for producing 3,5-Mepz$(CH_2)_2S(CH_2)_2S(CH_2)COOEt$ according to Example 5.
Figure 6:
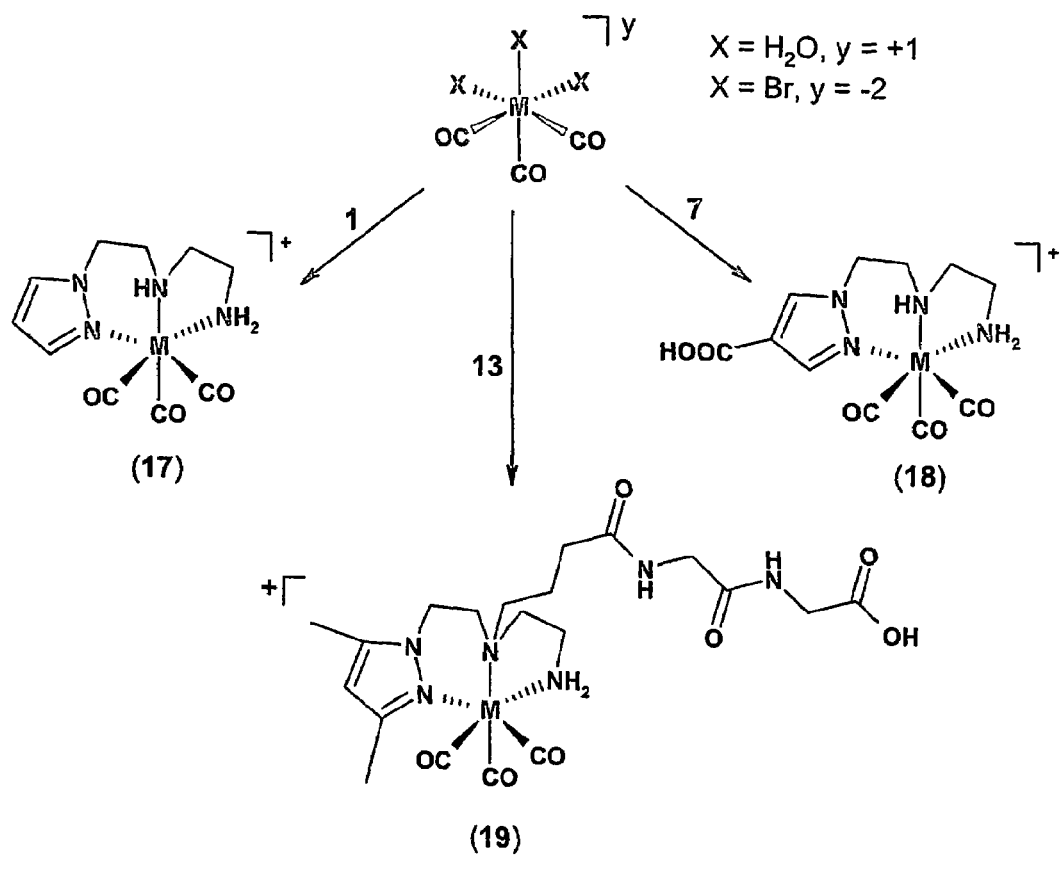
FIG. 6 is a schematic of various Re and Tc complexes produced according to Example 6.

The present invention will be further illustrated in the FIGS. 3-6, which are solely intended to clarify the invention. This family of ligands led to thermodynamically stable complexes and the versatility of the backbone is an important factor for tuning the physico-chemical properties of the compounds and obviously its pharmacokinetics. In FIG. 6, some of the Re and Tc complexes referred as examples are schematically represented.

Materials and Methods

1. Synthesis of 2-[2-(pyrazol-1-yl)ethylimino]ethylamine (pz(CH$_2$)$_2$NH(CH$_2$)$_2$NH$_2$) (1) (see FIG. 3)

A solution of 1-(2-bromoethyl)pyrazole [6d] (12 mmol) in tetrahydrofuran was added dropwise to a solution of ethylenediamine (0.24 mol) in water. The mixture was refluxed for 4 hours. The THF was removed under vacuum and the water phase was washed with dichloromethane. After drying under vacuum resulted a yellow oil which was formulated as pz(CH$_2$)$_2$NH(CH$_2$)$_2$NH$_2$ (1). Yield: 50%

$^1$H-NMR (D$_2$O): 7.53 (d, H(3)pz, 1H); 7.45 (d, H(5)pz, 1H); 6.23 (t, H(4)pz, 1H); 4.14 (t, CH2, 2H); 2.91 (t, CH$_2$, 2H); 2.77 (t, CH$_2$, 2H); 2.62 (t, CH$_2$, 2H).

2. Synthesis pz(CH$_2$)$_2$N[(CH$_2$)$_3$COOH](CH$_2$)$_2$NH$_2$ (4) (see FIG. 3)

2.1. BOC-ON Protection

A solution of 1 (1.1 g; 7 mmol) in DMF (20 ml) was cooled to 0° C. and a solution of BOC-ON (1.7 g; 7 mmol) in DMF (20 ml) was added dropwise. The reaction mixture was stirred for 3 hours at 0° C. The solvent was removed under vacuum and the solid residue was dissolved in water and washed with chloroform 3 times, yielding 2 as an oil. Yield: 68%.

$^1$H-NMR (D$_2$O): 7.55 (d, H(3)pz, 1H); 7.47 (d, H(5)pz, 1H); 6.24 (t, H(4)pz, 1H); 4.38 (t, CH$_2$, 2H); 3.40 (t, CH$_2$, 2H); 3.20 (t, CH$_2$, 2H); 2.99 (t, CH$_2$, 2H); 1.25 (s, CH$_3$, 9H).

2.2. Alkylation with ethyl 4-bromobutyrate, Hydrolysis and Deprotection

Compound 2 (757 mg; 3 mmol) was dissolved in 10 ml of acetonitrile. Potassium carbonate (829 mg; 6 mmol) and a catalytic amount of potassium iodide were added to the solution, and ethyl 4-bromobutyrate (858 ml, 16 mmol) was added dropwise. After refluxing for 3 days, the supernatant was separated by filtration and vacuum dried leading to 3. This compound (733 mg, 2 mmol) was dissolved in an aqueous solution of NaOH (800 mg, 20 mmol) and reacted for one day at room temperature. The solution was then neutralized with HCl 1N and vacuum dried. The solid residue was dissolved in methanol, the precipitating salts were filtered off, and the solvent was removed under vacuum, yielding a yellow/brown oil formulated as 4. Yield: (50%).

$^1$H-NMR ($D_2O$): 7.78 (d, H(3)pz, 1H); 7.64 (d, H(5)pz, 1H); 6.42 (t, H(4)pz, 1H); 4.36 (t, $CH_2$, 2H); 3.10 (t, $CH_2$, 2H); 3.02 (t, $CH_2$, 2H); 2.86 (t, $CH_2$, 2H); 2.64 (t, $CH_2$, 2H); 2.15 (t, $CH_2$, 2H); 1.68 (q, $CH_2$, 2H)

3. Synthesis (4-carboxylic)pz$(CH_2)_2$NH$(CH_2)_2$NH$_2$ (7) (see FIG. 3)

3.1. Ethyl N-2-hydroxyethyl-4-pyrazolecarboxylate (5)

Compound 5 was prepared using the classical approach for preparing pyrazoles [7]. Ethyl 2-formyl-3-oxopropionate (2.80 g; 20 mmol) was dissolved in 20 ml of ethanol and cooled to 0° C. 2-Hydroxyethylhydrazine (1.44 g; 20 mmol) was dissolved in 100 ml of ethanol and was added dropwise to the solution of ethyl 2-formyl-3-oxopropionate. The reaction mixture was left overnight at room temperature. The solvent was vacuum removed yielding a yellow oil. Yield: 95%

$^1$H-NMR ($CDCl_3$): 7.93 (s, H(3)pz, 1H); 7.91 (s, H(5)pz, 1H); 4.30-4.22 (m, $CH_2$+$OCH_2$, 5H); 3.99 (t, $CH_2$, 2H); 1.30 (t, $CH_3$, 3H).

3.2. Ethyl N-(2-p-toluenesulfonylethyl)-4-pyrazolecarboxylate (6)

Ethyl N-2-hydroxyethyl-4-pyrazolecarboxylate (5) (2.76 g, 15 mmol) and p-toluenesulfonylchloride (2.85 g, 15 mmol) were suspended in a solution of acetone (15 ml) and water (15 ml) and cooled to 0° C. A solution of NaOH (0.6 g, 15 mmol) in water (10 ml) was added dropwise for 15 min. The mixture was then allowed to reach the room temperature and was vigorously stirred overnight. The acetone was evaporated and the aqueous solution was extracted 3 times with chloroform, yielding a yellow oil. Yield: 60%

$^1$H-NMR ($CDCl_3$): 7.82 (s, H(3)pz, 1H); 7.76 (s, H(5)pz, 1H); 7.61 (d, H(ph), 2H); 7.26 (d, H(ph), 2H); 4.35 (q, $OCH_2$, 2H); 4.24 (t, $CH_2$, 2H); 2.15 (s, $CH_3$, 3H); 1.33 (t, $CH_2$, 2H).

Compound 7 was prepared as follows. Ethylenediamine (16 ml; 0.24 mol) was dissolved in a solution of NaOH (9.6 g; 0.24 mol) in water (20 ml). A solution of Ethyl N-(2-p-toluenesulfonylethyl)-4-pyrazolecarboxylate (6) (4.06 g; 12 mmol) in THF (10 ml) was added dropwise to the ethylenediamine solution. The reaction mixture was refluxed for 24 hours. After that, the solvent was vacuum removed and the product was purified by column chromatography in silica-gel (eluent:methanol-NH$_3$/methanol (50:50)), yielding a dark yellow solid. Yield: 50%.

$^1$H-NMR ($D_2O$): δ 7.80 (s, H(3)pz, 1H); 7.64 (s, H(5)pz, 1H); 4.27 (t, $CH_2$, 2H); 3.24 (t, $CH_2$, 2H); 3.11-3.00 (m, 2$CH_2$, 4H). IV (KBr) (v/cm$^{-1}$): 1690 (C=O).

4. Synthesis of 3,5-Mepz$(CH_2)_2$N[$(CH_2)_3$GlyGlyOEt)]$(CH_2)_2$NH$_2$ (13) (FIG. 4)

4.1. BOC-ON Protection (9)

Compound 8 (3.41 g, 18.71 mmol) [4c] was dissolved in THF (25 mL) and cooled to a temperature between –10° C. and 0° C. BOC-ON (4.60 g, 18.71 mmol) in THF (20 ml) was added dropwise and the reaction mixture was stirred for 2 h at 0° C., resulting in the complete conversion of 8 as monitored by TLC ($R_f$=0.5, 100% MeOH). The reaction mixture was then warmed to room temperature and partitioned between a saturated aqueous $Na_2CO_3$ solution and dichloromethane. The organic layer was separated, dried over anhydrous $MgSO_4$, filtered, and concentrated under reduced pressure to afford the product 9 in quantitative yield (by $^1$H-NMR), as a highly viscous colorless oil. This product was used in the next step without further purification.

$^1$H-NMR ($CDCl_3$): δ5.76 (s, pyrazol, 1H), 5.08 (s br., NH, 1H), 4.04 (t, $CH_2$, 2H), 3.18 (m, $CH_2$, 2H), 2.99 (t, $CH_2$, 2H), 2.72 (t, $CH_2$, 2H), 2.18 (s, $CH_3$, 3H), 2.20 (s, $CH_3$, 3H), 1.40 (s, $C(CH_3)_3$, 9H).

4.2. Synthesis of 3,5-Me$_2$pz$(CH_2)_2$N[$(CH_2)_3$COOH]$(CH_2)_2$NHBOC (11)

To a stirred solution of the crude product 9 (1.02 g) in $CH_3CN$ (15 mL), ethyl 4-bromobutyrate (1.4 g, 7.20 mmol), $K_2CO_3$ (1.00 g, 7.20 mmol) and a catalytic amount of KI were added. The obtained suspension was allowed to react under vigorous stirring for 11 days, being the reaction monitored by TLC ($R_f$ product=0.4, 10% MeOH/$CH_2Cl_2$). After elimination of the white solids in suspension by filtration, the solvent was evaporated in vacuum and a pale-yellow viscous oil was obtained. The crude product was chromatographed on an appropriate column of silica gel with 75-100% ethyl acetate/hexane (gradient) to afford 10 as a pale-yellow viscous oil, which solidifies on standing for several days at room temperature. Yield: 0.73 g (51% yield).

A solution of 10 (4.6 g, 11.60 mmol) in THF (190 mL) and aqueous NaOH (8.3 mL of a 14 N NaOH solution, 116.0 mmol) was refluxed for 8 h. The reaction was monitored by TLC ($R_f$ product=0.2, 10% MeOH/$CH_2Cl_2$). After neutralization with HCl 4N (pH 6-7), the THF/$H_2O$ solution was evaporated to dryness under reduced pressure. The crude product was chromatographed on an appropriate column of silica gel with 10-50% MeOH/$CHCl_3$ (gradient) to afford 11 as an highly viscous colorless oil, which crystallizes on standing after several days. Yield: 2.82 g (66%).

Compound 10: $^1$H-NMR ($CDCl_3$): δ 5.75 (s, pyrazol, 1H), 4.09 (q, $CH_2$, 2H), 3.98 (s br., $CH_2$, 2H), 3.08 (s br., $CH_2$, 2H), 2.78 (s br., $CH_2$, 2H), 2.45-2.51 (m, $CH_2$, 4H), 2.23 (s, $CH_3$, 3H), 2.18 (m, $CH_3$, $CH_2$, 5H), 1.63 (s br., $CH_2$, 2H), 1.41 (s, $C(CH_3)_3$, 9H), 1.23 (t, $CH_3$, 3H).

Compound 11: $^1$H-NMR ($CDCl_3$): δ 5.81 (s, pyrazol, 1H), 4.93 (s br., NH, 1H) 4.12 (t br., $CH_2$, 2H), 3.04 (q br., $CH_2$, 2H), 2.86 (t br., $CH_2$, 2H), 2.58-2.64 (m, $CH_2$, 4H), 2.42 (t, $CH_2$, 2H), 2.24 (s, $CH_3$, 3H), 2.19 (s, $CH_3$, 3H), 1.79 (m, $CH_2$, 2H), 1.40 (s, $C(CH_3)_3$, 9H).

Compound 3,5-Me$_2$pz $(CH_2)_2$N [$(CH_2)_3$CONHGlyGlyOEt]$(CH_2)_2$NH$_2$ (13) was prepared as follows (see FIG. 4).

To a solution of 11 (1.51 g, 4.09 mmol) in $CH_3CN$ (48 mL) were added GlyGly ethyl ester hydrochloride (0.57 g, 4.09 mmol), triethylamine (1.24 g, 12.27 mmol), and HBTU (1.55 g, 4.09 mmol). The reaction mixture was stirred 20 h at room temperature under nitrogen. The reaction was monitored by TLC ($R_f$ product=0.8, 20% MeOH/$CH_2Cl_2$). The solvent was evaporated and the crude product obtained was purified by chromatography on an appropriate silica gel column with 3-5% MeOH/CHCl$_3$ (gradient) to afford 12 as a viscous colorless oil. Yield: 1.23 g (59%).

A solution of 3,5-Me$_2$pz(CH$_2$)$_2$N[(CH$_2$)$_3$CONHGlyGlyOEt](CH$_2$)$_2$NHBOC (12) (1.23 g, 2.41 mmol) in CH$_2$Cl$_2$/TFA (25 mL/4.1 mL) was allowed to react for 2 h. The reaction was monitored by TLC (R$_f$=0.4, 20% MeOH/CH$_2$Cl$_2$) . The solvent and the TFA were evaporated under reduced pressure and a highly viscous pale-yellow oil was obtained. This oil was dissolved in water, neutralized with NaOH 1N (pH 7-8) and the solvent evaporated to dryness. TLC: R$_f$=0.2, 20% MeOH/CH$_2$Cl$_2$ The compound was further purified by chromatography on an appropriate silica gel column with 20-40% MeOH/CHCl$_3$ (gradient) to afford 13 as a viscous colorless oil. Yield: 0.97 g (98%).

Compound 12: $^1$H-NMR (CDCl$_3$): δ 8.66 (s br., NH, 1H), 7.00 (s br., NH, 1H), 5.80 (s, pyrazol, 1H), 4.91 (s br., NH, 1H) 4.15 (q., CH$_2$, 2H), 4.04 (s br., CH$_2$, 2H), 3.97 (d, CH$_2$, 2H), 3.90 (d, CH$_2$, 2H), 2.89 (s br., CH$_2$, 2H), 2.69 (s br., CH$_2$, 2H), 2.51 (s br., CH$_2$, 2H), 2.39 (s br., CH$_2$, 2H), 2.30 (s br., CH$_2$, 2H), 2.20 (s, CH$_3$, 3H), 2.18 (s, CH$_3$, 3H), 1.74 (s br., CH$_2$, 2H), 1.38 (s, C(CH$_3$)$_3$, 9H), 1.23 (t, CH$_3$, 3H).

Compound 13: $^1$H-NMR (CD30D): δ 5.84 (s, pyrazol, 1H), 4.17 (q, CH$_2$, 2H), 4.06 (t, CH$_2$, 2H), 3.91 (d, CH$_2$, 4H), 2.97 (t, CH$_2$, 2H), 2.71-2.80 (m, CH$_2$, 4H), 2.51 (t, CH$_2$, 2H), 2.25 (s, CH$_3$, 3H), 2.15 (s, CH$_3$, 3H), 2.12 (t, CH$_2$, 2H), 1.66 (m, CH$_2$, 2H), 1.25 (t, CH$_3$, 3H).

5. Synthesis of 3,5-Mepz(CH$_2$)$_2$S(CH$_2$)$_2$S(CH$_2$)COOEt (16) (FIG. 5)

5.1 Synthesis of 3,5-Mepz(CH$_2$)$_2$S(CH$_2$)$_2$OH (14)

0.70 ml (10 mmol) of HSCH$_2$CH$_2$OH were mixed with 0.40 g (10 mmol) of NaOH, in water, and the solution was refluxed for 5 min. To this solution, 2.78 g (10 mmol) of N-(2-p-toluenesulfonylethyl)-3,5-dimethylpyrazole dissolved in tetrahydrofuran (THF) were added dropwise at room temperature, followed by gentle reflux for 3 hr. The mixture was extracted with chloroform from which, after drying under vacuum, were recovered 1.62 g of 14 as a yellow oil (8.10 mmol, 81%).

Compound 14: $^1$H-NMR (CDCl$_3$): 5.67 (s, pz-H, 1H); 4.39 (s, OH, 1H); 4.03 (t, CH$_2$, 2H); 3.60 (t, CH$_2$, 2H); 2.83 (t, CH$_2$, 2H); 2.50 (t, CH$_2$, 2H); 2.14 (s, CH$_3$, 3H); 2.09 (s, CH$_3$, 3H).

5.2 Synthesis of 3,5-Mepz(CH$_2$)$_2$S(CH$_2$)$_2$Br (15)

0.19 ml (2 mmol) of PBr$_3$ were added to 14 (0.40 g, 2 mmol) dissolved in chloroform, and the resulting solution was refluxed for 24 hours under N$_2$. The mixture was treated with 20 ml of 10% NaHCO$_3$ solution. The organic phase was separated and chloroform removed under vacuum, yielding 0.329 g of 15 as a yellow oil (1.25 mmol, 63%).

$^1$H-NMR (CD$_{Cl3}$): 5.82 (s, pz-H, 1H); 4.15 (t, CH$_2$, 2H); 3.36 (t, CH$_2$, 2H); 3.00 (t, CH$_2$, 2H); 2.70 (t, CH$_2$, 2H); 2.26 (s, CH$_3$, 3H); 2.23 (s, CH$_3$, 3H).

Under N$_2$, dry ethanol was added to metallic sodium (0.15 g, 4.56 mmol), and the mixture was stirred at room temperature until complete conversion to sodium ethoxide. To this mixture an ethanolic solution of ethyl 2-mercaptoacetate (0.50 ml, 4.56 mmol) was added dropwise, followed by addition of 1.20 g (4.56 mmol) of 3,5-Mepz(CH$_2$)$_2$S(CH$_2$)$_2$Br (15) in ethanol. The reaction mixture was stirring overnight at room temperature. After this time, the solvent was removed under vacuum and the resulting oil was dissolved in chloroform. After washing with water, the organic phase was dried under vacuum yielding 1.00 g of 16 as a yellow oil (3.3 mmol, 72.4%).

Compound 16: $^1$H-NMR (CDCl$_3$): 5.82 (s, pz-H, 1H); 4.14 (m, CH$_2$, CH$_2$—COO, 4H); 3.25 (s, CH$_2$, 2H); 2.92 (t, CH$_2$, 2H); 2.75 (t, CH$_2$, 2H); 2.57 (t, CH$_2$, 2H); 2.2 (s, CH$_3$, 3H); 2.16 (s, CH$_3$, 3H); 1.25 (t, CH$_3$, 3H).

6. Re and Tc Compounds (see FIG. 6)

6.1. Synthesis of [Re(CO)$_3$(κ$^3$-pz(CH$_2$)$_2$NH(CH$_2$)$_2$NH$_2$)]Br (17a)

100 mg (0.130 mmol) of (NEt$_4$)$_2$[ReBr$_3$(CO)$_3$] were mixed with 20 mg (0.130 mmol) of the compound 1 (pz(CH$_2$)$_2$NH(CH$_2$)$_2$NH$_2$) in water, and the solution was refluxed for 2 hours. The volume was then reduced under vacuum, and the mixture was left at 4° C. until a white solid precipitated. Yield: >90% by $^1$H-NMR $^1$H-NMR (D$_2$O): 7.82 (d, H(3)pz, 1H); 7.76 (d, H(5)pz, 1H); 6.54 (s br, NH, 1H); 6.39 (t, H(4)pz, 1H); 4.86 (s, largo, NH$_2$, 1H); 4.43 (m, CH$_2$, 1H); 4.16 (m, CH$_2$, 1H); 3.94 (s, largo, NH$_2$, 1H); 3.50 (m, CH$_2$, 1H); 2.87 (m, CH$_2$, 1H); 2.71 (m, CH$_2$, 2H); 2.48 (m, CH$_2$, 1H); 2.08 (m, CH$_2$, 1H).

6.2. Synthesis of [$^{99m}$Tc(CO)$_3$(κ$^3$-pz(CH$_2$)$_2$NH(CH$_2$)$_2$NH$_2$)]+ (17b)

100 µl of a solution of compound 1 (pz(CH$_2$)$_2$NH(CH$_2$)$_2$NH$_2$) 10$^{-4}$ M was added to 1 ml of a solution of [$^{99m}$Tc(OH)$_3$(CO)$_3$]+ (1-2 mCi) in phosphate buffer. The solution was incubated for 30 min at 100° C. and then analyzed by HPLC. The radiochemical purity was >90%.

6.3. Synthesis of [Re(CO)$_3$(κ$^3$-(4-carboxylic acid)pz(CH$_2$)$_2$NH(CH$_2$)$_2$NH$_2$)]Br (18a)

100 mg (0.130 mmol) of (NEt$_4$)$_2$[ReBr$_3$(CO)$_3$] were mixed with 26 mg (0.130 mmol) of compound 7, in water, and the solution was refluxed for 2 hours. The volume was then reduced under vacuum, and the mixture was left at 4° C. until a white solid precipitated. Yield: >90% by $^1$H-NMR $^1$H-NMR (D$_2$O): δ 8.22 (s, H(3)pz, 1H); 8.20 (s, H(5)pz, 1H); 6.62 (s, largo, NH, 1H); 4.94 (s, largo, NH$_2$, 1H); 4.43 (m, CH$_2$, 1H); 4.25 (m, CH$_2$, 1H); 4.05 (s, largo, NH$_2$, 1H); 3.52 (m, CH$_2$, 1H); 2.92 (m, CH$_2$, 1H); 2.76 (m, CH$_2$, 2H); 2.53 (m, CH$_2$, 1H); 2.14 (m, CH$_2$, 1H).

IV (KBr) (v/cm$^{-1}$): 2010 (C≡O); 1885 (C≡O); 1690 (C=O ligando)

6.4. Synthesis of [Re(CO)$_3$(κ$^3$-3,5-Me$_2$pz(CH$_2$)$_2$N(CH$_2$)$_2$(glygly)NH$_2$)]Br (19a)

100 mg (0.130 mmol) of (NEt4)$_2$[ReBr$_3$(CO)$_3$] were mixed with 53 mg (0.130 mmol) of the ligand 13, in water, and the solution was refluxed overnight. Yield: 100% by $^1$H-NMR $^1$H-NMR (D$_2$O): δ 6.04 (s, H(4)pz, 1H); 5.05 (s, br, NH$_2$, 1H); 4.36-4.31 (m, CH$_2$, 1H); 4.16-4.04 (m, CH$_2$, 1H); 3.88 (s, NHCH$_2$CO, 2H); 3.84 (s, NHCH$_2$CO, 2H); 3.65 (s, br, NH$_2$, 1H); 3.53 (m, CH$_2$, 1H); 3.30 (m, CH$_2$, 2H); 2.86 (m, CH$_2$, 1H); 2.74 (m, CH$_2$, 2H); 2.57 (m, CH$_2$, 1H); 2.40 (m, CH$_2$, 1H); 2.31 (m, CH$_2$, 1H); 2.73 (s, CH$_3$, 3H); 2.16 (s, CH$_3$, 3H); 2.10 (m, CH$_2$, 1H); 1.95 (m, CH$_2$, 1H).

6.5. Synthesis of [$^{99m}$Tc(CO)$_3$($\kappa^3$-3,5-Me$_2$pz(CH$_2$)$_2$N(CH$_2$)$_2$(glygly)NH$_2$)]$^+$ (19b)

100 ml of a solution of 13 (10$^{-3}$ M) was added to 1 ml of a solution of [$^{99m}$Tc(OH)$_3$(CO)$_3$]$^+$ (1-2 mCi) in phosphate buffer. The solution was incubated for 1 h at 100° C. and then analysed by HPLC. The radiochemical purity was >90%.

Figure 7:
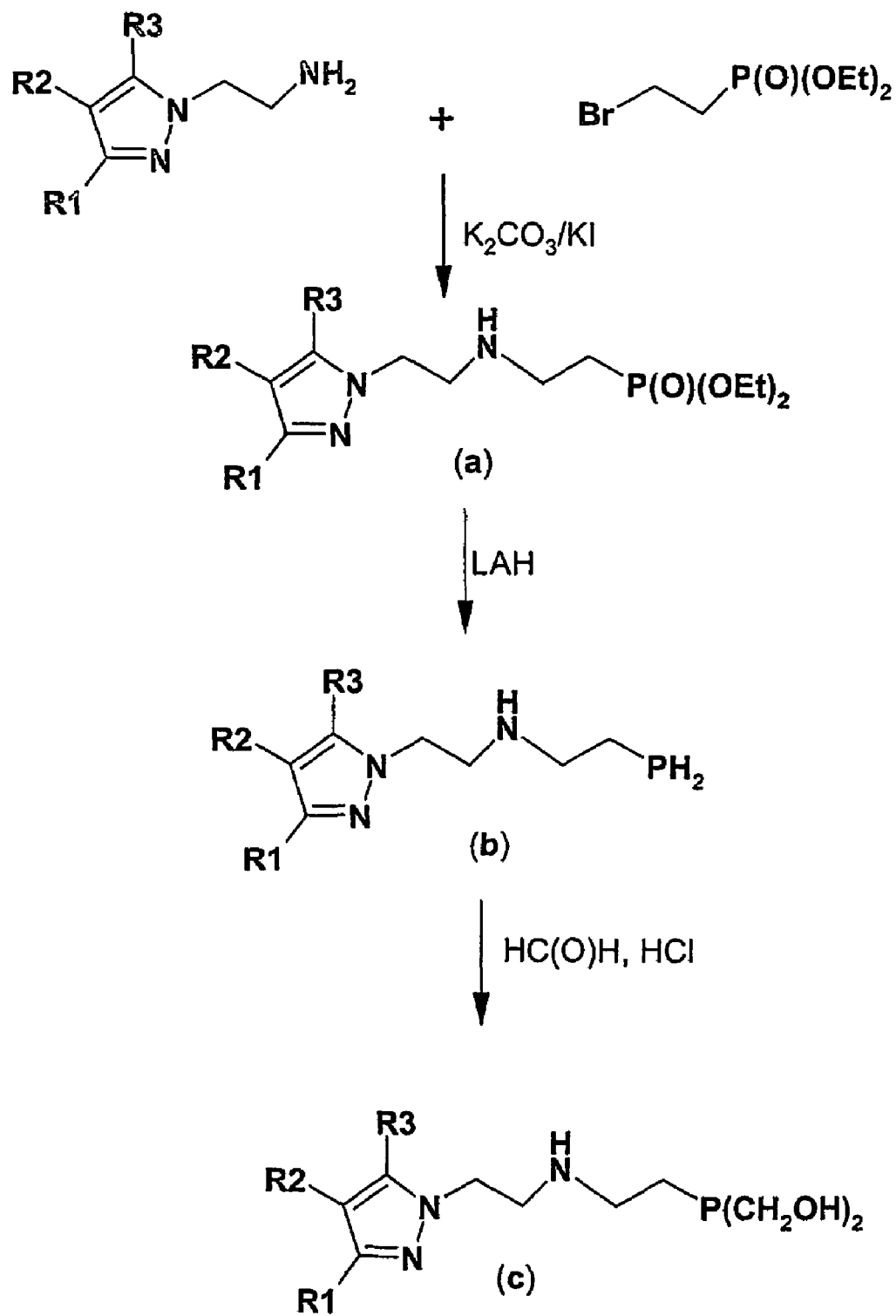
FIG. 7 is a schematic of a synthesis route for producing pyrazolyl-aminophosphines according to Example 7.

7. Synthesis of pyrazolyl-aminophosphines (FIG. 7)

The preparation of the pyrazolyl-aminophosphines of the invention involves alkylation of 1-(2-aminoethyl)pyrazoles with (2-bromoethyl)phosphonic acid diethyl esther, yielding a pyrazole-amino-phosphonate derivative (compound a). Reduction of compound a with lithium aluminium hydride (LAH) affords a primary phoshine (compound b) which is then converted to the final chelator (compound c) by treatment with formaldehyde in acidic medium (Katti et al., J. Am. Chem. Soc. 122, 1554 (2000).

Figure 8:
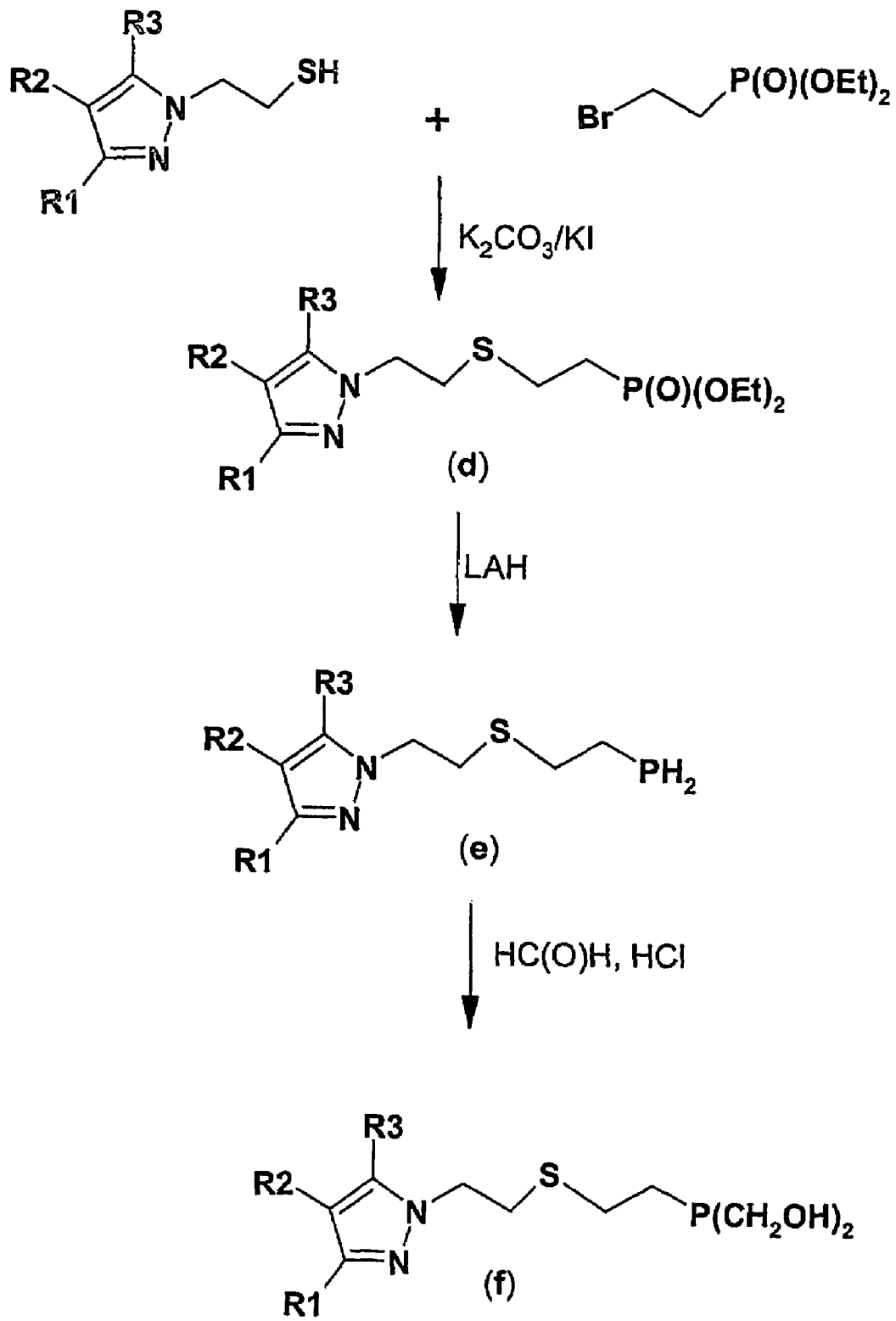
FIG. 8 is a schematic of a synthesis route for producing pyrazolyl-thioetherphosphines according to Example 8.

8. Synthesis of pyrazolyl-thioetherphosphines (FIG. 8)

The preparation of pyrazolyl-thioetherphosphines of the invention involves reaction of 1-(2-mercaptoethyl)pyrazoles with (2-bromoethyl)phosphonic acid diethyl esther yielding a pyrazole-thioether-phosphonate derivative (compound d) (Katti et al., Angew. Chem. Int. Ed. 38, 2020 (1999). Reduction of compound d with lithium aluminium hydride, followed by treatment of the resulting primary phoshine (compound e) with formaldehyde in acidic medium affords the final chelator (compound f).

REFERENCES

[1] a) Alberto et al WO 98/48848,
b) Alberto et al., WO 00/50086,
c) Alberto et al., WO 01/00637
d) Alberto et al, U.S. Pat. No. 6,344,178 B1
[2] a) Hilger et al, U.S. Pat. No. 6,488,909 B1.
[3] a) Alberto et al, Polyhedron 17 (1998) 1303
b) Alberto et al., J. Med. Chem. 41 (1998) 4429
c) Alberto et al, J. Am. Chem. Soc. 121 (1999) 6076
d) Alberto et al, J. Nucl. Med. 40 (1999) 1913
e) Schibli et al, Nucl. Med. and Biol. 26 (1999) 711
f) Alberto et al, Bioconjugate Chem. 11 (2000) 414
g) Alberto et al, Bioconjugate Chem. 11 (2000) 345
h) Alberto et al., Chem. Eur. Journal 7 (2001) 1868
i) Alberto et al, Angew. Chem. Int. Ed. 40 (2001) 3062
j) Alberto et al, Bioconjugate Chem. 13 (2002) 750.
[4] a) Santos et al, J. Am. Chem. Soc. 122 (2000) 11240
b) Santos et al., Inorg. Chem. 40 (2001) 5147
c) Santos et al, J. Chem. Soc. Dalton Trans. (2002) 4714.
[5] a) Valliant et al, Inorg Chem. Commun. 41 (2002) 628
b) Valliant et al, Inorg Chem. 41 (2002) 6417
[6] a) Sorrell et al, Inorg. Chem. 22 (1983) 1883
b) Driessen et al. J. Chem. Soc. Dalton Trans. (1992) 481
c) Parkin et al., Inorg. Chem. 35 (1996) 2415
d) Ballesteros et al., Bioorganic and Medicinal Chem. 7 (1999) 517.
e) Bouwman et al., Inorg. Chim. Acta (2000) 183
[7] Holzer et al, J. Heterocyclic Chem. 130 (1993) 865

The invention claimed is:

1. Chelating agent of the general formula:

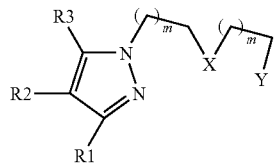

wherein m is 0 or 1;
X is NR$_4$ or S;
Y is SR$_5$, NHR$_6$ or P(R$_5$)$_2$;
R$_1$ and R$_3$ are the same or different and are selected from H, alkyl or aryl;
R$_2$ is H, COOH, NHR$_6$ or (CH$_2$)$_n$COOR$_6$;
R$_4$ is H, alkyl, aryl, (CH$_2$)$_n$COOR$_6$ or (CH$_2$)$_n$OR$_6$;
R$_5$ is H, alkyl, aryl, (CH$_2$)$_n$COOR$_6$ or (CH$_2$)$_n$OR$_6$;
R$_6$ is H, alkyl or aryl;
n is 1, 2, 3, 4, 5, 6, 7, 8, 9 or 10; and
wherein at least one of R$_1$, R$_3$, R$_4$, R$_5$, and R$_6$ is phenyl or benzyl.

2. Chelating agent of the general formula:

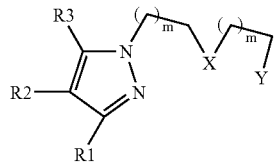

wherein m is 0 or 1;
X is NR$_4$ or S;
Y is SR$_5$, NHR$_4$ or P(R$_5$)$_2$;
R$_1$, and R$_3$ are the same or different and are selected from H, alkyl or aryl, wherein at least one of R$_1$ and R$_3$ is aryl;
R$_2$ is H, COOH, NHR$_6$ or (CH$_2$)$_n$COOR$_6$;
R$_4$ is H, alkyl, aryl, (CH$_2$)$_n$COOR$_6$ or (CH$_2$)$_n$OR$_6$;
R$_5$ is H, alkyl, aryl, (CH$_2$)$_n$COOR$_6$ or (CH$_2$)$_n$OR$_6$;
R$_6$ is H, a biomolecule, alkyl or aryl; and
n is 1, 2, 3, 4, 5, 6, 7, 8, 9 or 10.

3. A metal complex comprising the chelating agent of claim 1.

4. Chelating agent as claimed in claim 2, wherein R$_6$ is a biomolecule.

5. Chelating agent as claimed in claim 4, wherein the biomolecule is selected from amino acids, peptides, proteins, oligonucleotides, polynucleotides, and sugars.

6. Chelating agent as claimed in claim 4, wherein the biomolecule is selected from the group consisting of antibodies and ligands of tumor receptors.

7. Chelating agent as claimed in claim 4, wherein the biomolecule is selected from the group consisting of CCK, thioglucose, glucosamine, somatostatin, neurotensin, bombesin, annexin, interleukins, growth factors, steroid hormones and molecules binding to GPIIb/IIIa receptors.

8. Chelating agent as claimed in claim 4, wherein the biomolecule is selected from the group consisting of glucose, thioglucose, and neurotransmitters.

9. Chelating agent as claimed in claim 4, wherein the biomolecule is an inhibitor of the tyrosine kinase activity.

10. The chelating agent as claimed in claim 1, wherein when R$_1$=R$_3$=CH$_3$, R$_2$, R$_4$ and R$_5$ are not all three H.

11. The chelating agent as claimed in claim 2, wherein when $R_1$ or $R_3$ is $CH_3$, $R_2$, $R_4$ and $R_5$ are not all three H.

12. Chelating agent as claimed in claim 1, wherein alkyl is a $C_1$ alkyl, $C_2$ alkyl, $C_3$ alkyl, $C_4$ alkyl, $C_5$ alkyl or $C_6$ alkyl.

13. Chelating agent as claimed in claim 12, wherein alkyl is methyl, ethyl, n-propyl, isopropyl, n-butyl, isobutyl, s-butyl, t-butyl, n-pentyl, isopentyl, neopentyl, n-hexyl, isohexyl (2-methylpentyl), neohexyl (2,2-dimethylbutyl), 3-methyl pentyl, 2,3-dimethylbutyl.

14. Chelating agent as claimed in claim 1, wherein n is 2, 3, 4, 5 or 6.

15. Chelating agent as claimed in claim 2, wherein alkyl is a $C_1$ alkyl, $C_2$ alkyl, $C_3$ alkyl, $C_4$ alkyl, $C_5$ alkyl or $C_6$ alkyl.

16. Chelating agent as claimed in claim 15, wherein alkyl is methyl, ethyl, n-propyl, isopropyl, n-butyl, isobutyl, s-butyl, t-butyl, n-pentyl, isopentyl, neopentyl, n-hexyl, isohexyl (2-methylpentyl), neohexyl (2,2-dimethyl butyl), 3-methylpentyl, 2,3-dimethylbutyl.

17. Chelating agent as claimed in claim 2, wherein n is 2, 3, 4, 5 or 6.

* * * * *